United States Patent
Swayze et al.

(10) Patent No.: US 9,445,816 B2
(45) Date of Patent: Sep. 20, 2016

(54) CIRCULAR STAPLER WITH SELECTABLE MOTORIZED AND MANUAL CONTROL

(71) Applicant: Ethicon Endo-Surgery, Inc., Cincinnati, OH (US)

(72) Inventors: Jeffrey S. Swayze, Hamilton, OH (US); Chester O. Baxter, III, Loveland, OH (US); Frederick E. Shelton, IV, Hillsboro, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 694 days.

(21) Appl. No.: 13/716,308

(22) Filed: Dec. 17, 2012

(65) Prior Publication Data

US 2014/0166727 A1 Jun. 19, 2014

(51) Int. Cl.
| | |
|---|---|
| *A61B 17/10* | (2006.01) |
| *A61B 17/04* | (2006.01) |
| *A61B 17/115* | (2006.01) |
| *A61B 17/00* | (2006.01) |

(52) U.S. Cl.
CPC .. *A61B 17/1155* (2013.01); *A61B 2017/00115* (2013.01); *A61B 2017/00393* (2013.01); *A61B 2017/00398* (2013.01); *A61B 2017/00734* (2013.01)

(58) Field of Classification Search
CPC .......................... A61B 17/068; A61B 17/1155
USPC ............................................ 227/175.1–182.1
See application file for complete search history.

(56) References Cited

U.S. PATENT DOCUMENTS

| | | | |
|---|---|---|---|
| 4,805,823 A | 2/1989 | Rothfuss | |
| 4,930,674 A * | 6/1990 | Barak | A61B 17/02 227/179.1 |
| 5,205,459 A | 4/1993 | Brinkerhoff et al. | |
| 5,271,544 A | 12/1993 | Fox et al. | |
| 5,275,322 A | 1/1994 | Brinkerhoff et al. | |
| 5,285,945 A | 2/1994 | Brinkerhoff et al. | |

(Continued)

FOREIGN PATENT DOCUMENTS

| | | |
|---|---|---|
| EP | 1 813 211 | 8/2007 |
| EP | 1 982 657 | 10/2008 |

(Continued)

OTHER PUBLICATIONS

U.S. Appl. No. 13/688,951, filed Nov. 29, 2012.

(Continued)

*Primary Examiner* — Robert Long
(74) *Attorney, Agent, or Firm* — Frost Brown Todd LLC

(57) ABSTRACT

An apparatus is operable to clamp, cut, and staple tissue. The apparatus includes a stapling head assembly, a shaft assembly coupled to the stapling head assembly, and an actuator handle assembly coupled to the shaft assembly. The stapling head assembly is operable to clamp tissue, cut tissue, and staple tissue in response to rotation imparted by a single rotary drive shaft extending through the shaft assembly. The actuator handle assembly includes a motor positioned within a motor housing, a rotation knob, and a selection assembly. The rotation knob is coupled to a proximal end of the motor housing. The rotation knob is configured to translate between a proximal position and a distal position. The selection assembly is operable to select between motorized operation of the apparatus or manual operation of the apparatus, based on the longitudinal position of the rotation knob.

19 Claims, 22 Drawing Sheets

(56) References Cited

U.S. PATENT DOCUMENTS

| | | | |
|---|---|---|---|
| 5,292,053 | A | 3/1994 | Bilotti et al. |
| 5,333,773 | A | 8/1994 | Main et al. |
| 5,350,104 | A | 9/1994 | Main et al. |
| 5,415,334 | A | 5/1995 | Williamson, IV et al. |
| 5,417,700 | A * | 5/1995 | Egan .................. A61B 17/0469 |
| | | | 606/103 |
| 5,465,895 | A | 11/1995 | Knodel et al. |
| 5,533,661 | A | 7/1996 | Main et al. |
| 5,597,107 | A | 1/1997 | Knodel et al. |
| 5,632,432 | A | 5/1997 | Schulze et al. |
| 5,673,840 | A | 10/1997 | Schulze et al. |
| 5,704,534 | A | 1/1998 | Huitema et al. |
| 5,711,472 | A * | 1/1998 | Bryan .............. A61B 17/07207 |
| | | | 227/175.1 |
| 5,814,055 | A | 9/1998 | Knodel et al. |
| 6,783,524 | B2 | 8/2004 | Anderson et al. |
| 6,978,921 | B2 | 12/2005 | Shelton, IV et al. |
| 7,000,818 | B2 | 2/2006 | Shelton, IV et al. |
| 7,143,923 | B2 | 12/2006 | Shelton, IV et al. |
| 7,252,660 | B2 * | 8/2007 | Kunz .............. A61B 17/00234 |
| | | | 606/1 |
| 7,303,108 | B2 | 12/2007 | Shelton, IV |
| 7,367,485 | B2 | 5/2008 | Shelton, IV et al. |
| 7,380,695 | B2 | 6/2008 | Doll et al. |
| 7,380,696 | B2 | 6/2008 | Shelton, IV et al. |
| 7,404,508 | B2 | 7/2008 | Smith et al. |
| 7,434,715 | B2 | 10/2008 | Shelton, IV et al. |
| 7,721,930 | B2 | 5/2010 | McKenna et al. |
| 7,794,475 | B2 | 9/2010 | Hess et al. |
| 7,959,050 | B2 | 6/2011 | Smith et al. |
| 8,752,749 | B2 | 6/2014 | Moore et al. |
| 2005/0267555 | A1 * | 12/2005 | Marnfeldt .......... A61B 17/3417 |
| | | | 607/116 |
| 2008/0029576 | A1 * | 2/2008 | Shelton ............ A61B 17/07207 |
| | | | 227/176.1 |
| 2008/0169327 | A1 * | 7/2008 | Shelton ............ A61B 17/07207 |
| | | | 227/176.1 |
| 2008/0255413 | A1 | 10/2008 | Zemlok et al. |
| 2008/0308607 | A1 * | 12/2008 | Timm .............. A61B 17/07207 |
| | | | 227/176.1 |
| 2009/0030437 | A1 * | 1/2009 | Houser .......... A61B 17/320092 |
| | | | 606/169 |
| 2010/0198244 | A1 * | 8/2010 | Spivey ........... A61B 17/320016 |
| | | | 606/174 |
| 2010/0211053 | A1 * | 8/2010 | Ross .................... A61B 17/068 |
| | | | 606/1 |
| 2011/0022032 | A1 | 1/2011 | Zemlok et al. |
| 2011/0208174 | A1 * | 8/2011 | Baust .................... A61B 18/02 |
| | | | 606/21 |
| 2011/0208236 | A1 * | 8/2011 | Ward .................... A61B 10/06 |
| | | | 606/205 |
| 2012/0223121 | A1 * | 9/2012 | Viola .................. A61B 17/072 |
| | | | 227/175.1 |
| 2012/0228358 | A1 * | 9/2012 | Zemlok ................ A61B 17/072 |
| | | | 227/176.1 |
| 2013/0090642 | A1 * | 4/2013 | Shadduck ............ A61B 18/085 |
| | | | 606/33 |
| 2014/0000411 | A1 | 1/2014 | Shelton, IV et al. |
| 2014/0031819 | A1 * | 1/2014 | Dycus ................ A61B 18/1445 |
| | | | 606/47 |
| 2014/0166718 | A1 * | 6/2014 | Swayze ............. A61B 17/1155 |
| | | | 227/175.1 |

FOREIGN PATENT DOCUMENTS

| | | |
|---|---|---|
| EP | 2 0044 888 | 4/2009 |
| EP | 2 055 243 | 5/2009 |

OTHER PUBLICATIONS

U.S. Appl. No. 13/688,992, filed Nov. 29, 2012.
U.S. Appl. No. 13/693,430, filed Dec. 4, 2012.
U.S. Appl. No. 13/693,455, filed Dec. 4, 2012
U.S. Appl. No. 13/706,827, filed Dec. 6, 2012.
U.S. Appl. No. 13/716,313, filed Dec. 17, 2012.
U.S. Appl. No. 13/716,318, filed Dec. 17, 2012.
U.S. Appl. No. 13/716,323, filed Dec. 17, 2012.
International Search Report dated Jul. 17, 2014 for Application No. PCT/US2013/075240.
International Written Opinion dated Jul. 17, 2014 for Application No. PCT/US2013/075240, 10 pages.

* cited by examiner

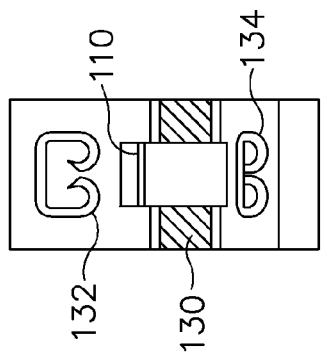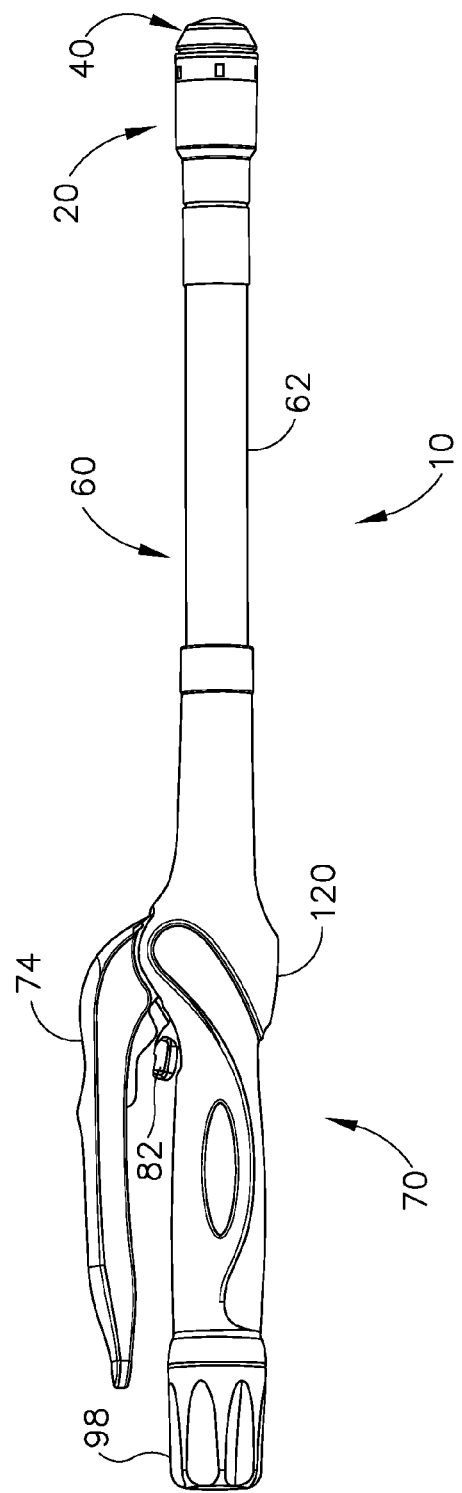

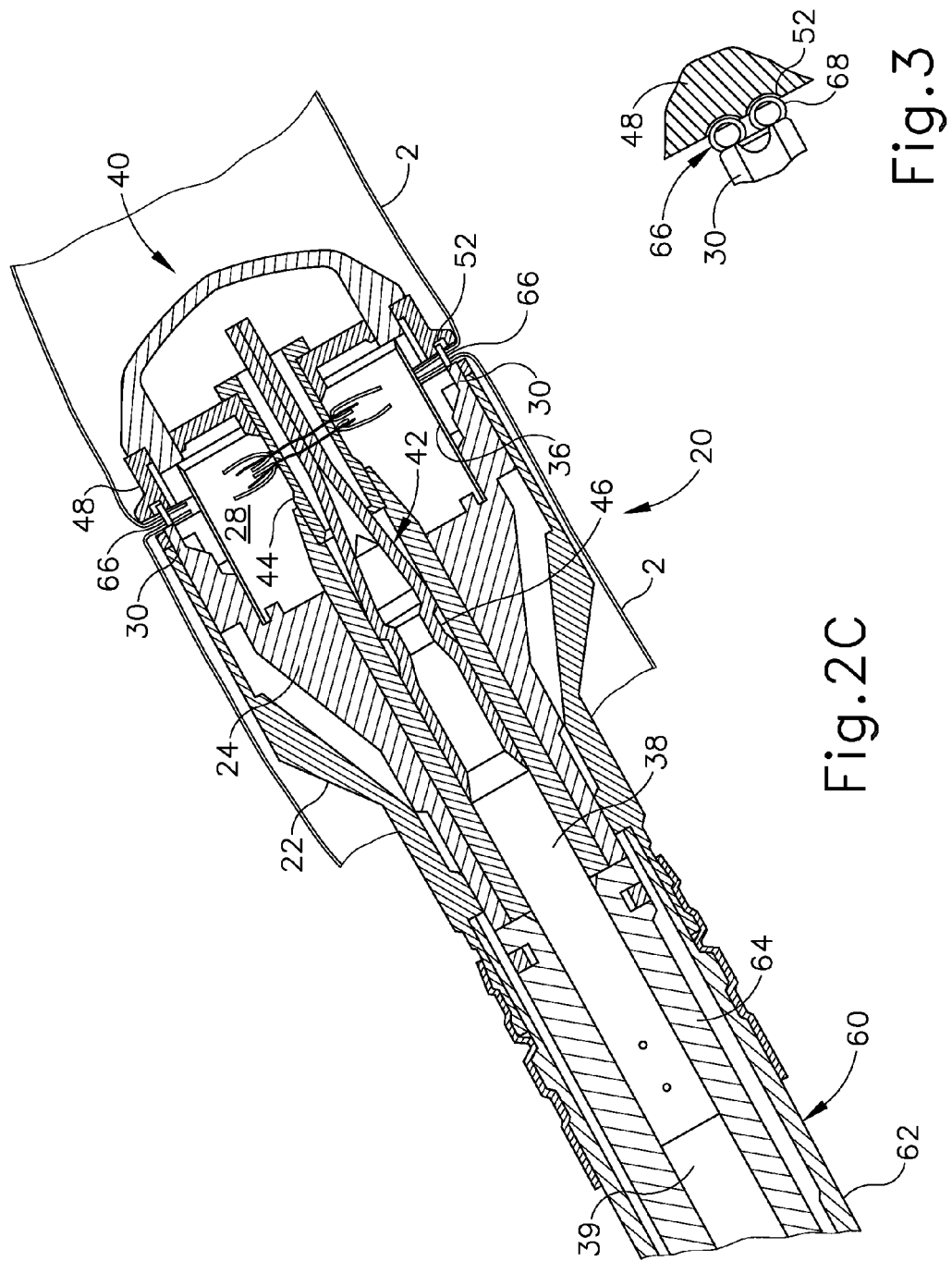

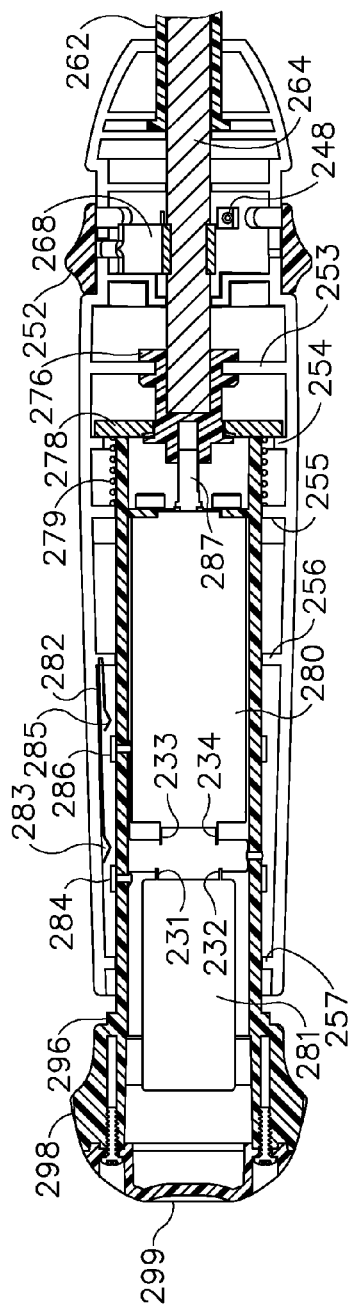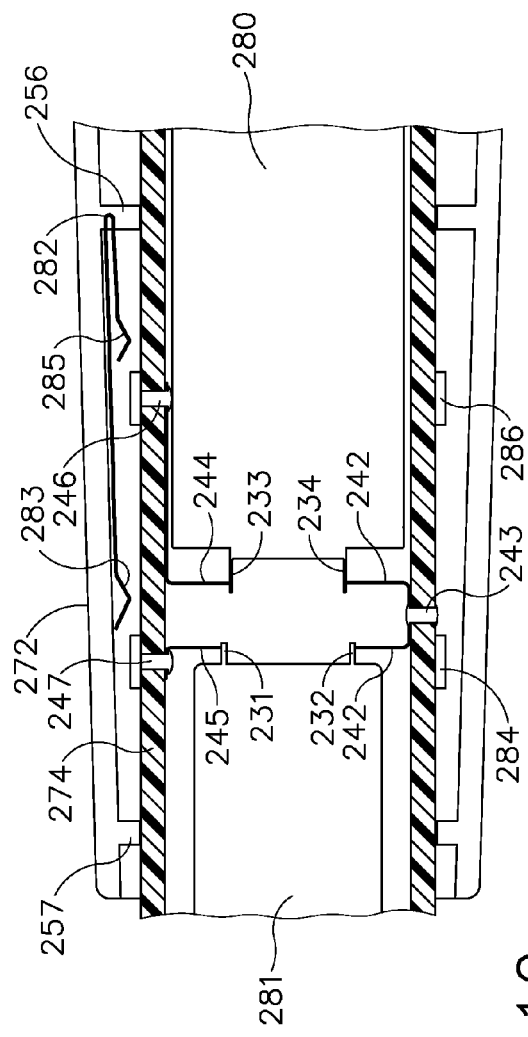

CIRCULAR STAPLER WITH SELECTABLE MOTORIZED AND MANUAL CONTROL

BACKGROUND

In some settings, a surgeon may want to position a surgical instrument through an orifice of the patient and use the instrument to adjust, position, attach, and/or otherwise interact with tissue within the patient. For instance, in some surgical procedures, portions of the gastrointestinal tract may be cut and removed to eliminate undesirable tissue or for other reasons. Once the desired tissue is removed, the remaining portions may need to be recoupled together. One such tool for accomplishing these anastomotic procedures is a circular stapler that is inserted through a patient's orifice.

Examples of circular surgical staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996. The disclosure of each of the above-cited U.S. Patents is incorporated by reference herein. Some such staplers are operable to clamp down on layers of tissue, cut through the clamped layers of tissue, and drive staples through the layers of tissue to substantially seal the severed layers of tissue together near the severed ends of the tissue layers, thereby joining two severed ends of an anatomical lumen.

Merely additional other exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; and U.S. Pat. No. 7,721,930, entitled "Disposable Cartridge with Adhesive for Use with a Stapling Device," issued May 25, 2010. The disclosure of each of the above-cited U.S. Patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 1 depicts a side elevation view of an exemplary circular stapling surgical instrument;

FIG. 2C depicts an enlarged longitudinal cross-sectional view of the stapling head assembly of FIG. 2A showing an exemplary staple driver and blade in a fired position;

FIG. 3 depicts an enlarged partial cross-sectional view of an exemplary staple formed against the anvil;

FIG. 6 depicts an diagrammatic view of the indicator window of FIG. 5 showing an exemplary indicator bar and exemplary corresponding staple representations;

FIG. 9 depicts a cross sectional view of the handle assembly of the instrument of FIG. 7;

FIG. 10 depicts an enlarged, partial cross sectional view of the motor and battery assemblies of FIG. 7;

Figure 2A:
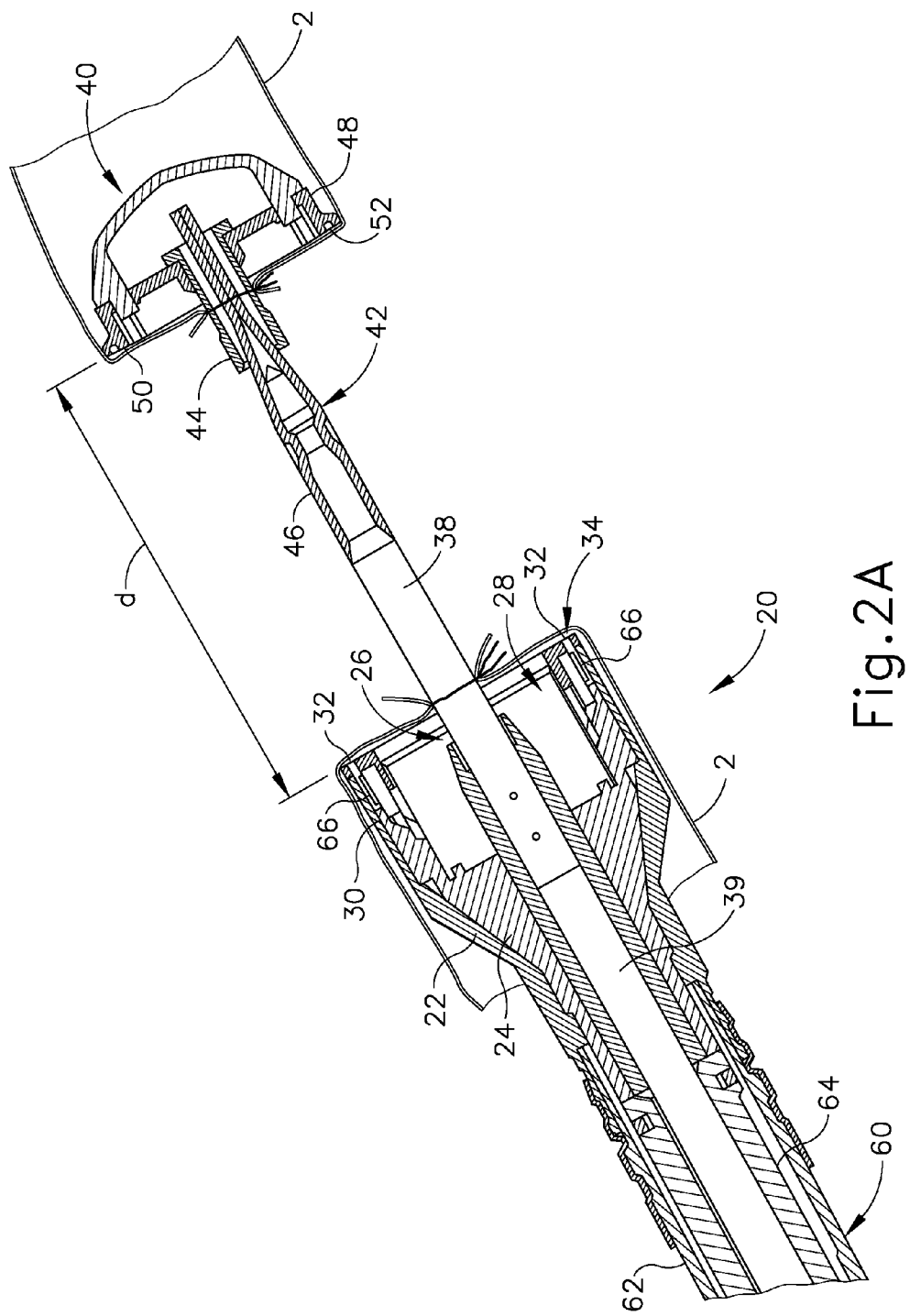
FIG. 2A depicts an enlarged longitudinal cross-section view of an exemplary stapling head assembly of the instrument of FIG. 1 showing an exemplary anvil in an open position.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

FIGS. 1-6 depict an exemplary circular surgical stapling instrument (10) having a stapling head assembly (20), a shaft assembly (60), and an actuator handle assembly (70), each of which will be described in more detail below. Shaft assembly (60) extends distally from actuator handle assembly (70) and stapling head assembly (20) is coupled to a distal end of shaft assembly (60). In brief, actuator handle assembly (70) is operable to actuate a staple driver (24) of stapling head assembly (20) to drive a plurality of staples (66) out of stapling head assembly (20). Staples (66) are bent to form completed staples by an anvil (40) that is attached at the distal end of instrument (10). Accordingly, tissue (2), shown in FIGS. 2A-2C, may be stapled utilizing instrument (10).

In the present example, instrument (10) comprises a closure system and a firing system. The closure system comprises a trocar (38), a trocar actuator (39), and a rotating knob (98). An anvil (40) may be coupled to a distal end of trocar (38). Rotating knob (98) is operable to longitudinally translate trocar (38) relative to stapling head assembly (20), thereby translating anvil (40) when anvil (40) is coupled to trocar (38), to clamp tissue between anvil (40) and stapling head assembly (20). The firing system comprises a trigger (74), a trigger actuation assembly (84), a driver actuator (64), and a staple driver (24). Staple driver (24) includes a knife (36) configured to sever tissue when staple driver (24) is actuated longitudinally. In addition, staples (66) are positioned distal to a plurality of staple driving members (30) of staple driver (24) such that staple driver (24) also drives staples (66) distally when staple driver (24) is actuated longitudinally. Thus, when trigger (74) is actuated and trigger actuation assembly (84) actuates staple driver (24) via driver actuator (64), knife (36) and members (30) substantially simultaneously sever tissue (2) and drive staples (66) distally relative to stapling head assembly (20) into tissue. The components and functionalities of the closure system and firing system will now be described in greater detail.

A. Exemplary Anvil

Figure 2B:
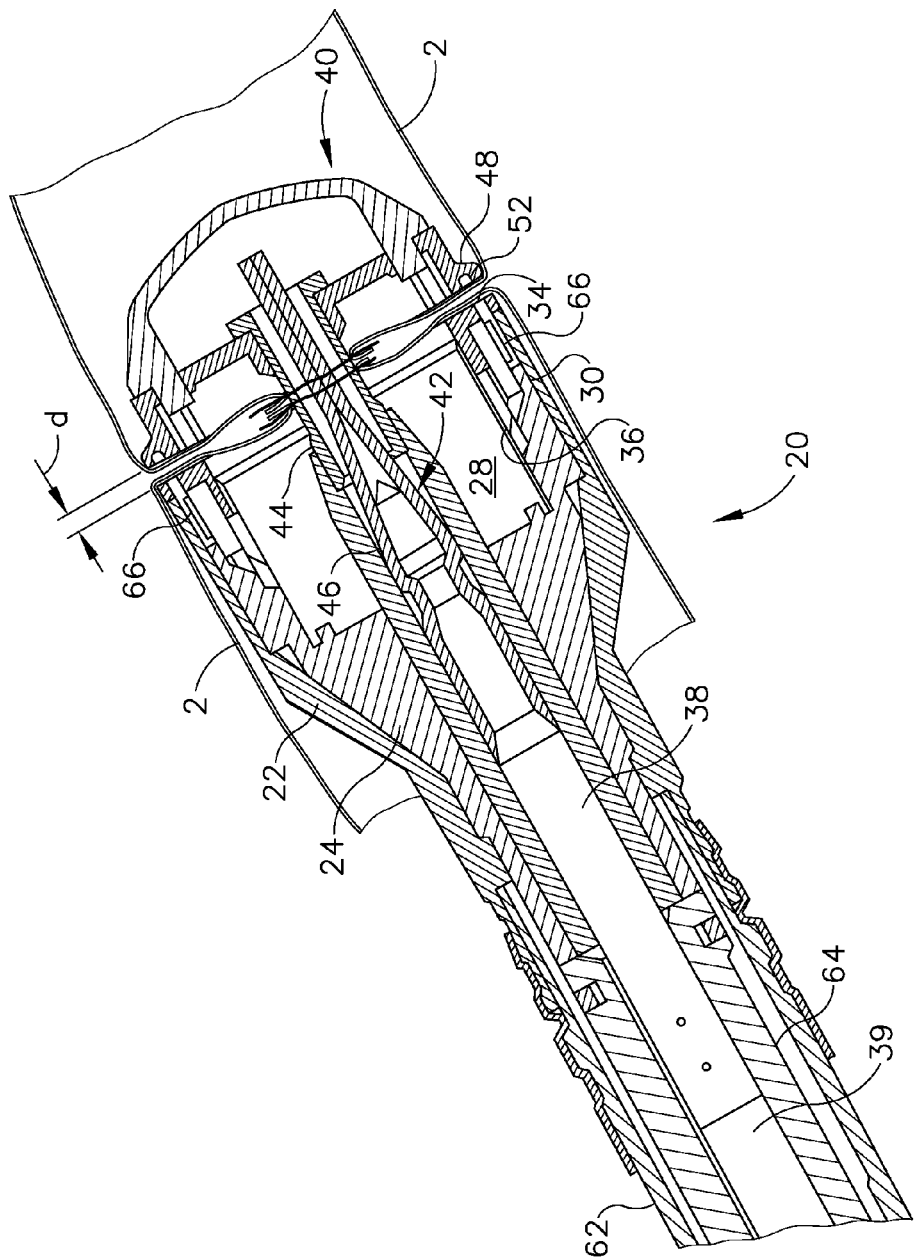
FIG. 2B depicts an enlarged longitudinal cross-sectional view of the stapling head assembly of FIG. 2A showing the anvil in a closed position.

As shown in FIGS. 1-2C, anvil (40) is selectively coupleable to instrument (10) to provide a surface against which staples (66) may be bent to staple material contained between stapling head assembly (20) and anvil (40). Anvil (40) of the present example is selectively coupleable to a trocar or pointed rod (38) that extends distally relative to stapling head assembly (20). Referring to FIGS. 2A-2C, anvil (40) is selectively coupleable via the coupling of a proximal shaft (42) of anvil (40) to a distal tip of trocar (38). Anvil (40) comprises a generally circular anvil head (48) and a proximal shaft (42) extending proximally from anvil head (48). In the example shown, proximal shaft (42) comprises a tubular member (44) having resiliently biased retaining clips (46) to selectively couple anvil (40) to trocar (38), though this is merely optional, and it should be understood that other retention features for coupling anvil (40) to trocar (38) may be used as well. For example, C-clips, clamps, threading, pins, adhesives, etc. may be employed to couple anvil (40) to trocar (38). In addition, while anvil (40) is described as selectively coupleable to trocar (38), in some versions proximal shaft (42) may include a one-way coupling feature such that anvil (40) cannot be removed from trocar (38) once anvil (40) is attached. Merely exemplary one-way features include barbs, one way snaps, collets, collars, tabs, bands, etc. Of course still other configurations for coupling anvil (40) to trocar (38) will be apparent to one of ordinary skill in the art in view of the teachings herein. For instance, trocar (38) may instead be a hollow shaft and proximal shaft (42) may comprise a sharpened rod that is insertable into the hollow shaft.

Anvil head (48) of the present example comprises a plurality of staple forming pockets (52) formed in a proximal face (50) of anvil head (48). Accordingly, when anvil (40) is in the closed position and staples (66) are driven out of stapling head assembly (20) into staple forming pockets (52), as shown in FIG. 2C, legs (68) of staples (66) are bent to form completed staples.

With anvil (40) as a separate component, it should be understood that anvil (40) may be inserted and secured to a portion of tissue (2) prior to being coupled to stapling head assembly (20). By way of example only, anvil (40) may be inserted into and secured to a first tubular portion of tissue (2) while instrument (10) is inserted into and secured to a second tubular portion of tissue (2). For instance, the first tubular portion of tissue (2) may be sutured to or about a portion of anvil (40), and the second tubular portion of tissue (2) may be sutured to or about trocar (38).

As shown in FIG. 2A, anvil (40) is then coupled to trocar (38). Trocar (38) of the present example is shown in a distal most actuated position. Such an extended position for trocar (38) may provide a larger area to which tissue (2) may be coupled prior to attachment of anvil (40). In addition, the extended position of trocar (38) may also provide for easier attachment of anvil (40) to trocar (38). Trocar (38) further includes a tapered distal tip. Such a tip may be capable of piercing through tissue and/or aiding the insertion of anvil (40) on to trocar (38), though the tapered distal tip is merely optional. For instance, in other versions trocar (38) may have a blunt tip. In addition, or in the alternative, trocar (38) may include a magnetic portion (not shown) which may attract anvil (40) towards trocar (38). Of course still further configurations and arrangements for anvil (40) and trocar (38) will be apparent to one of ordinary skill in the art in view of the teachings herein.

When anvil (40) is coupled to trocar (38), the distance between a proximal face of the anvil (40) and a distal face of stapling head assembly (20) defines a gap distance d. Trocar (38) of the present example is translatable longitudinally relative to stapling head assembly (20) via an adjusting knob (98) located at a proximal end of actuator handle assembly (70), as will be described in greater detail below. Accordingly, when anvil (40) is coupled to trocar (38), rotation of adjusting knob (98) enlarges or reduces gap distance d by actuating anvil (40) relative to stapling head assembly (20). For instance, as shown sequentially in FIGS. 2A-2B, anvil (40) is shown actuating proximally relative to actuator handle assembly (70) from an initial, open position to a closed position, thereby reducing the gap distance d and the distance between the two portions of tissue (2) to be joined. Once the gap distance d is brought within a predetermined range, stapling head assembly (20) may be fired, as shown in FIG. 2C, to staple and sever tissue (2) between anvil (40) and stapling head assembly (20). Stapling head assembly (20) is operable to staple and sever tissue (2) by a user pivoting a trigger (74) of actuator handle assembly (70), as will be described in greater detail below.

Figure 5:
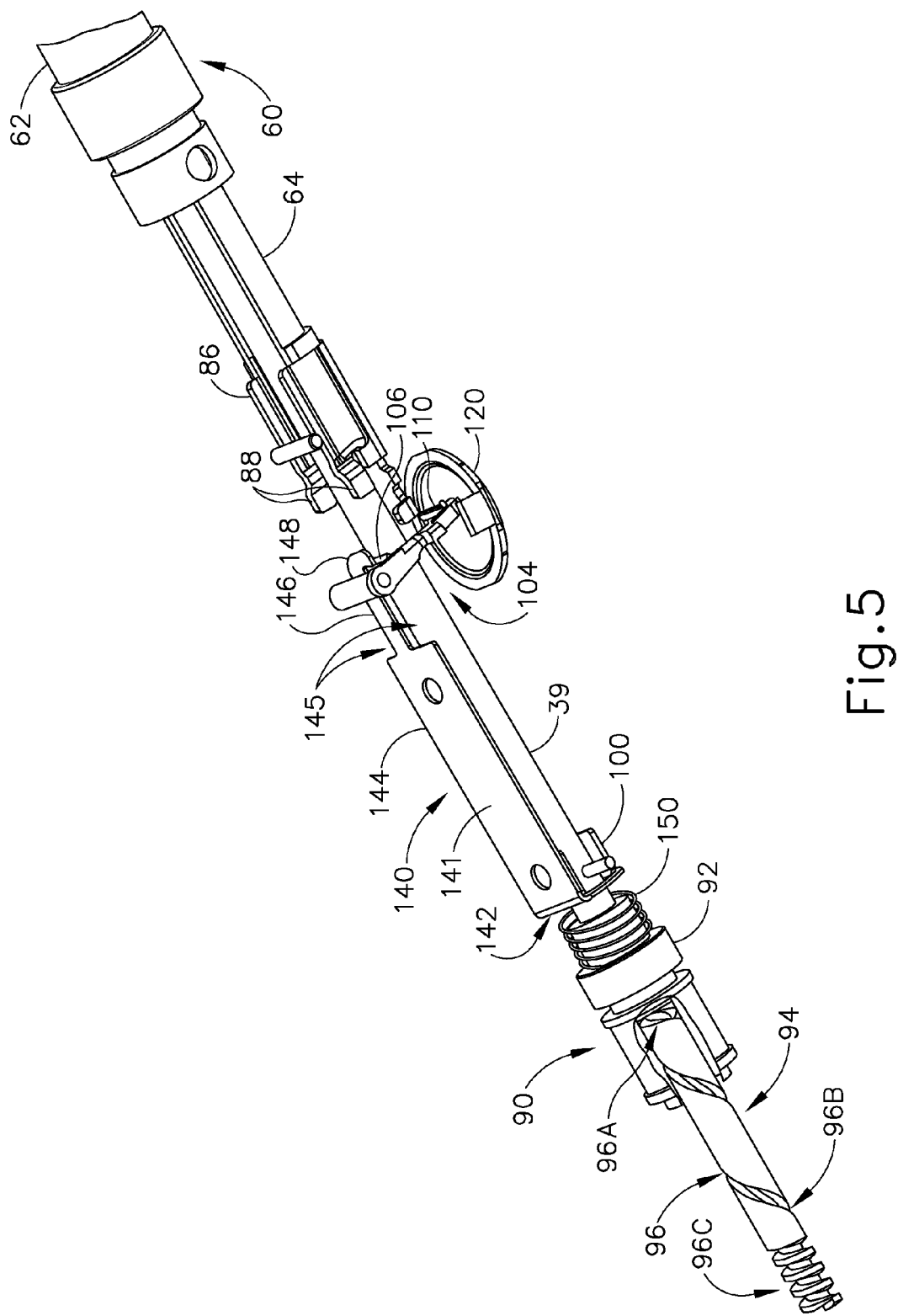
FIG. 5 depicts an enlarged partial perspective view of an exemplary indicator assembly of the surgical instrument of FIG. 1 showing an indicator window and indicator lever.

As noted above, gap distance d corresponds to the distance between anvil (40) and stapling head assembly (20). When instrument (10) is inserted into a patient, this gap distance d may not be easily viewable. Accordingly, a moveable indicator bar (110), shown in FIGS. 5-6, is provided to be visible through an indicator window (120) positioned opposite to trigger (74). Indicator bar (110) is operable to move in response to rotation of adjusting knob (98) such that the position of indicator bar (110) is representative of the gap distance d. As shown in FIG. 6, indicator window (120) further comprises a scale (130) which indicates that the anvil gap is within a desired operating range (e.g., a green colored region or "green zone") and a corresponding staple compression representation at each end of scale (130). By way of example only, as shown in FIG. 6, a first staple image (132) depicts a large staple height while a second staple image (134) depicts a small staple height. Accordingly, a user can view the position of the coupled anvil (40) relative to the stapling head assembly (20) via indicator bar (110) and scale (130). The user may then adjust the positioning of anvil (40) via adjusting knob (98) accordingly.

Referring back to FIGS. 2A-2C, a user sutures a portion of tissue (2) about tubular member (44) such that anvil head (48) is located within a portion of the tissue (2) to be stapled. When tissue (2) is attached to anvil (40), retaining clips (46) and a portion of tubular member (44) protrude out from tissue (2) such that the user may couple anvil (40) to trocar (38). With tissue (2) coupled to trocar (38) and/or another portion of stapling head assembly (20), the user attaches anvil (40) to trocar (38) and actuates anvil (40) proximally towards stapling head assembly (20) to reduce the gap distance d. Once instrument (10) is within the operating range, the user then staples together the ends of tissue (2), thereby forming a substantially contiguous tubular portion of tissue (2).

Anvil (40) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

B. Exemplary Stapling Head Assembly

Stapling head assembly (20) of the present example is coupled to a distal end of shaft assembly (60) and comprises a tubular casing (22) housing a slidable staple driver (24) and a plurality of staples (66) contained within staple pockets (32). Staples (66) and staple pockets (32) are disposed in a circular array about tubular casing (22). In the present example, staples (66) and staple pockets (32) are disposed in a pair of concentric annular rows of staples (66) and staple pockets (32). Staple driver (24) is operable to actuate longitudinally within tubular casing (22) in response to rotation of trigger (74) of actuator handle assembly (70). As shown in FIGS. 2A-2C, staple driver (24) comprises a flared cylindrical member having a trocar opening (26), a central recess (28), and a plurality of members (30) disposed circumferentially about central recess (28) and extending distally relative to shaft assembly (60). Each member (30) is configured to contact and engage a corresponding staple (66) of the plurality of staples (66) within staple pockets (32). Accordingly, when staple driver (24) is actuated distally relative to actuator handle assembly (70), each member (30) drives a corresponding staple (66) out of its staple pocket (32) through a staple aperture (34) formed in a distal end of tubular casing (22). Because each member (30) extends from staple driver (24), the plurality of staples (66) are driven out of stapling head assembly (20) at substantially the same time. When anvil (40) is in the closed position, staples (66) are driven into staple forming pockets (52) to bend legs (68) of the staples (66), thereby stapling the material located between anvil (40) and stapling head assembly (20). FIG. 3 depicts one merely exemplary staple (66) driven by a member (30) into a staple forming pocket (32) of anvil (40) to bend legs (68).

Staple driver (24) further includes a cylindrical knife (36) that is coaxial to trocar opening (26) and inset from staple pockets (32). In the present example, cylindrical knife (36) is disposed within central recess (28) to translate distally with staple driver (24). When anvil (40) is secured to trocar (38), as described above, anvil head (48) provides a surface against which cylindrical knife (36) cuts the material contained between anvil (40) and stapling head assembly (20). In some versions, anvil head (48) may include a recess (not shown) for cylindrical knife (36) to aid in cutting the material (e.g., by providing a cooperative shearing edge). In addition, or in the alternative, anvil head (48) may include one or more opposing cylindrical knives (not shown) offset from cylindrical knife (36) such that a scissor-type cutting action may be provided. Still other configurations will be apparent to one of ordinary skill in the art in view of the teachings herein. Stapling head assembly (20) is thus operable to both staple and cut tissue (2) substantially simultaneously in response to actuation by actuator handle assembly (70).

Of course stapling head assembly (20) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

As noted previously, staple driver (24) includes a trocar opening (26). Trocar opening (26) is configured to permit trocar (38) to longitudinally slide relative to stapling head assembly (20) and/or shaft assembly (60). As shown in FIGS. 2A-2C, trocar (38) is coupled to a trocar actuator (39) such that trocar (38) can be actuated longitudinally via rotation of rotating knob (98), as will be described in greater detail below in reference to actuator handle assembly (70). In the present example, trocar actuator (39) comprises an elongated, relatively stiff shaft coupled to trocar (38), though this is merely optional. In some versions, actuator (39) may comprise a longitudinally stiff material while permitting lateral bending such that portions of instrument (10) may be selectively bent or curved during use; or instrument (10) may include a preset bent shaft assembly (60). One merely exemplary material is nitinol. When anvil (40) is coupled to trocar (38), trocar (38) and anvil (40) are translatable via actuator (39) to adjust the gap distance d between anvil (40) and stapling head assembly (20). Still further configurations for actuator (39) to longitudinally actuate trocar (38) will be apparent to one of ordinary skill in the art in view of the teachings herein.

C. Exemplary Shaft Assembly

Stapling head assembly (20) and trocar (38) are positioned at a distal end of shaft assembly (60), as shown in FIGS. 2A-2C. Shaft assembly (60) of the present example comprises an outer tubular member (62) and a driver actuator (64). Outer tubular member (62) is coupled to tubular casing (22) of stapling head assembly (20) and to a body (72) of actuator handle assembly (70), thereby providing a mechanical ground for the actuating components therein. The proximal end of driver actuator (64) is coupled to a trigger actuation assembly (84) of actuator handle assembly (70), described below. The distal end of driver actuator (64) is coupled to staple driver (24) such that the rotation of trigger (74) longitudinally actuates staple driver (24). As shown in FIGS. 2A-2C, driver actuator (64) comprises a tubular member having an open longitudinal axis such that actuator (39) coupled to trocar (38) may actuate longitudinally within and relative to driver actuator (64). Of course it should be understood that other components may be disposed within driver actuator (64) as will be apparent to one of ordinary skill in the art in view of the teachings herein.

Shaft assembly (60) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

D. Exemplary Actuator Handle Assembly

Figure 4A:
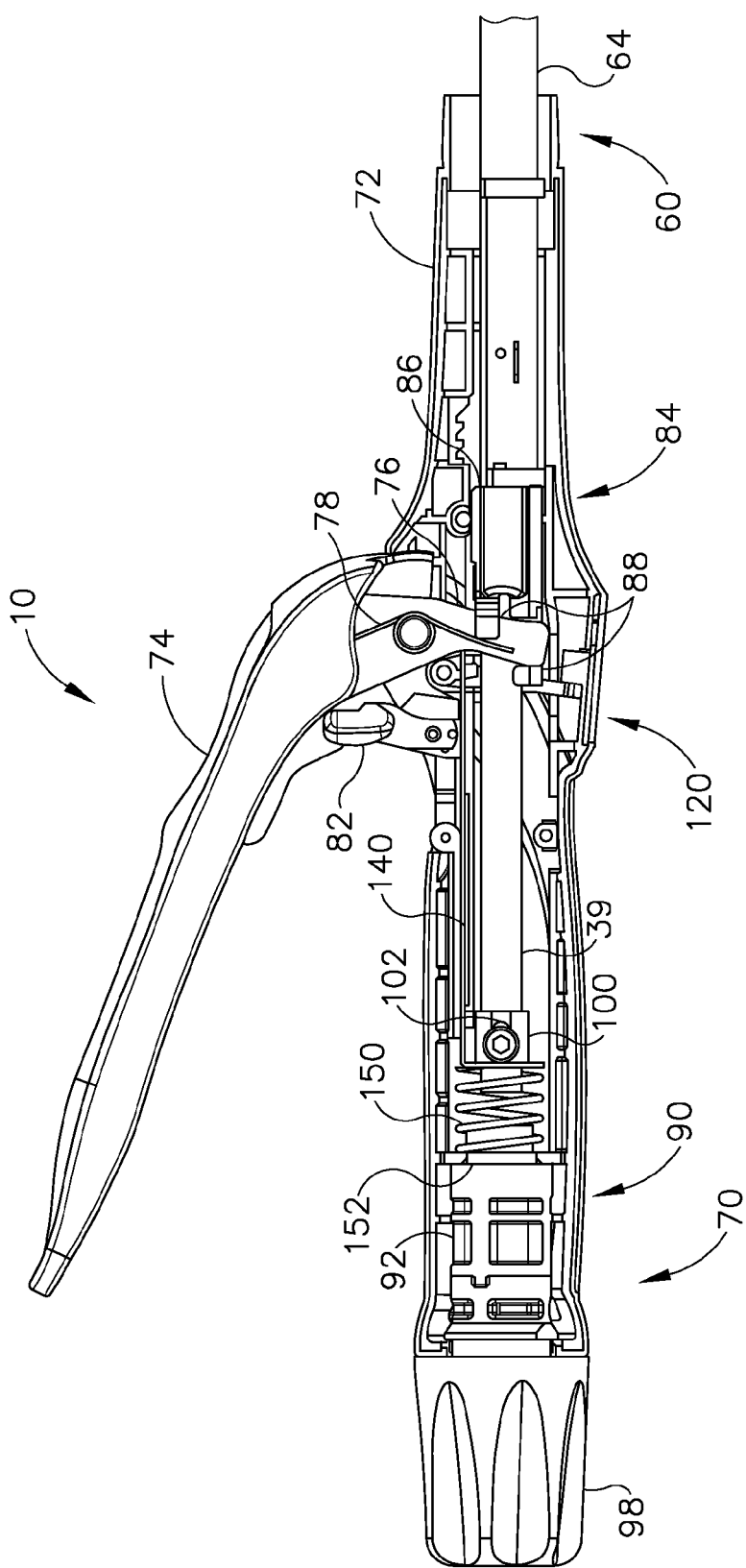
FIG. 4A depicts an enlarged side elevation view of an exemplary actuator handle assembly of the surgical instrument of FIG. 1 with a portion of the body removed, showing a trigger in an unfired position and a lockout feature in a locked position.
Figure 4B:
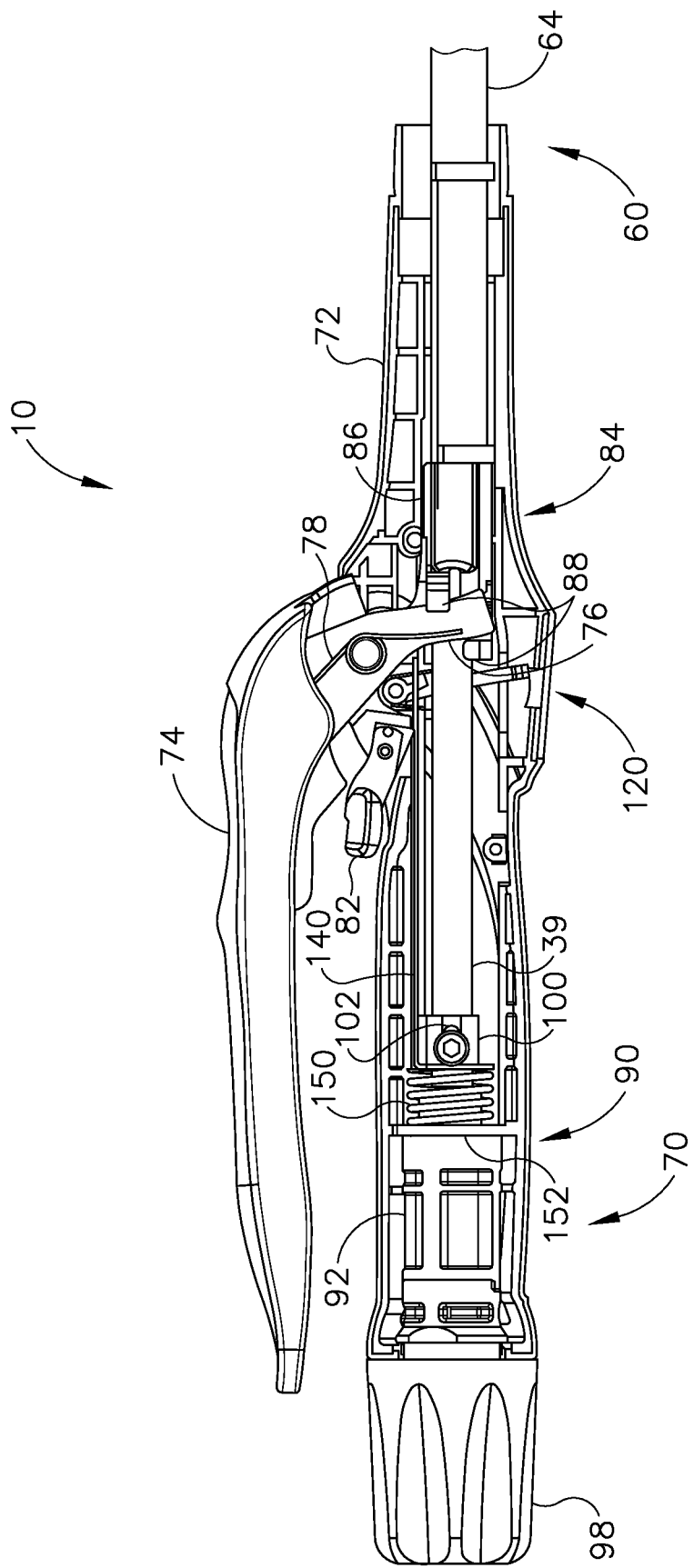
FIG. 4B depicts an enlarged side elevation view of the actuator handle assembly of FIG. 4A, showing the trigger in a fired position and the lockout feature in an unlocked position.

Referring now to FIGS. 4A-5, actuator handle assembly (70) comprises a body (72), a trigger (74), a lockout feature (82), a trigger actuation assembly (84), and a trocar actuation assembly (90). Trigger (74) of the present example is pivotably mounted to body (72) and is coupled to trigger actuation assembly (84) such that rotation of trigger (74) from an unfired position (shown in FIG. 4A) to a fired position (shown in FIG. 4B) actuates driver actuator (64) described above. A spring (78) is coupled to body (72) and trigger (74) to bias trigger (74) towards the unfired position. Lockout feature (82) is a pivotable member that is coupled to body (72). In a first, locked position, lockout feature (82) is pivoted upwards and away from body (72) such that lockout feature (82) engages trigger (74) and mechanically resists actuation of trigger (74) by a user. In a second, unlocked position, such as that shown in FIGS. 1 and 4B, lockout feature (82) is pivoted downward such that trigger (74) may be actuated by the user. Accordingly, with lockout feature (82) in the second position, trigger (74) can engage a trigger actuation assembly (84) to fire instrument (10).

As shown in FIGS. 4A-4B, trigger actuation assembly (84) of the present example comprises a slidable trigger carriage (86) engaged with a proximal end of driver actuator (64). Carriage (86) includes a set of tabs (88) on a proximal end of carriage (86) to retain and engage a pair of trigger arms (76) extending from trigger (74). Accordingly, when trigger (74) is pivoted, carriage (86) is actuated longitudinally and transfers the longitudinal motion to driver actuator (64). In the example shown, carriage (86) is fixedly coupled to the proximal end of driver actuator (64), though this is merely optional. Indeed, in one merely exemplary alternative, carriage (86) may simply abut driver actuator (64) while a distal spring (not shown) biases driver actuator (64) proximally relative to actuator handle assembly (70).

Trigger actuation assembly (84) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

Body (72) also houses a trocar actuation assembly (90) configured to actuate trocar (38) longitudinally in response to rotation of adjusting knob (98). As best shown in FIGS. 4A-5, trocar actuation assembly (90) of the present example comprises adjusting knob (98), a grooved shank (94), and a sleeve (92). Grooved shank (94) of the present example is located at a distal end of trocar actuator (39), though it should be understood that grooved shank (94) and trocar actuator (39) may alternatively be separate components that engage to transmit longitudinal movement. Adjusting knob (98) is rotatably supported by the proximal end of body (72)

and is operable to rotate sleeve (92) that is engaged with grooved shank (94) via an internal tab (not shown). Grooved shank (94) of the present example comprises a continuous groove (96) formed in the outer surface of grooved shank (94). Accordingly, when adjusting knob (98) is rotated, the internal tab rides within groove (96) and grooved shank (94) is longitudinally actuated relative to sleeve (92). Since grooved shank (94) is located at the distal end of trocar actuator (39), rotating adjusting knob (98) in a first direction advances trocar actuator (39) distally relative to actuator handle assembly (70). Accordingly, the gap distance d between anvil (40) and stapling head assembly (20) is increased. By rotating adjusting knob (98) in the opposite direction, trocar actuator (39) is actuated proximally relative to actuator handle assembly (70) to reduce the gap distance d between anvil (40) and stapling head assembly (20). Thus, trocar actuation assembly (90) is operable to actuate trocar (38) in response to rotating adjustment knob (98). Of course other configurations for trocar actuation assembly (90) will be apparent to one of ordinary skill in the art in view of the teachings herein.

Groove (96) of the present example comprises a plurality of different portions (96A, 96B, 96C) that have a varying pitch or number of grooves per axial distance. The present groove (96) is divided into a distal portion (96A), a middle portion (96B) and a proximal portion (96C). As shown in FIG. 5, distal portion (96A) comprises a fine pitch or a high number of grooves over a short axial distance of grooved shank (94) such that a large number of rotations of adjusting knob (98) are required to traverse the short axial distance. Middle portion (96B) comprises a section with comparably coarser pitch or fewer grooves per axial distance such that relatively few rotations are required to traverse a long axial distance. Accordingly, the gap distance d may be quickly reduced through relatively few rotations of adjusting knob (98). Proximal portion (96C) of the present example is substantially similar to distal portion (96A) and comprises a fine pitch or a high number of grooves over a short axial distance of grooved shank (94) such that a large number of rotations are required to traverse the short axial distance. Proximal portion (96C) of the present example is positioned within sleeve (92) when anvil (40) is substantially near to stapling head assembly (20) such that indicator bar (110) moves within indicator window (120) along scale (130) to indicate that the anvil gap is within a desired operating range, as will be described in more detail below. Accordingly, when the tab is within proximal portion (96C) of groove (96), each rotation of adjusting knob (98) may reduce the gap distance d by a small amount to provide for fine tuning.

Trocar actuation assembly (90) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

In the example shown in FIGS. 4A-4B, a U-shaped clip (100) is attached to an intermediate portion of trocar actuator (39) located distally of grooved shank (94). In the present example, an extension of trocar actuator (39) engages a slot in the housing of handle assembly (70) to prevent trocar actuator (39) from rotating about its axis when adjusting knob (98) is rotated. In some other versions, U-shaped clip (100) engages with a portion of body (72) to substantially prevent trocar actuator (39) from rotating about its axis when adjusting knob (98) is rotated. U-shaped clip (100) of the present example further includes an elongated slot (102) on each of its opposite sides for receiving an attachment member, such as a screw, bolt, pin, clip, etc., to selectively adjust the longitudinal position of elongated slot (102) of U-shaped clip (100) relative to trocar actuator (39) for purposes of calibrating indicator bar (110) relative to scale (130).

As shown in FIG. 5, actuator handle assembly (70) further includes an indicator bracket (140) configured to engage and pivot an indicator (104). Indicator bracket (140) of the present example is slidable relative to body (72) along a pair of slots formed on body (72). Indicator bracket (140) comprises a rectangular plate (144), an indicator arm (146), and an angled flange (142). Angled flange (142) is formed at the proximal end of rectangular plate (144) and includes an aperture (not shown) to slidable mount onto trocar actuator (39) and/or grooved shank (94). A coil spring (150) is interposed between flange (142) and a boss (152) to bias flange (142) against U-shaped clip (100). Accordingly, when U-shaped clip (100) actuates distally with trocar actuator (39) and/or grooved shank (94), coil spring (150) urges indicator bracket (140) to travel distally with U-shaped clip (100). In addition, U-shaped clip (100) urges indicator bracket (140) proximally relative to boss (152) when trocar actuator (39) and/or grooved shank (94) translate proximally, thereby compressing coil spring (150). Of course, it should be understood that in some versions indicator bracket (140) may be fixedly attached to trocar actuator (39) and/or grooved shank (94).

In the present example, a portion of lockout feature (82) abuts a surface (141) of indicator bracket (140) when indicator bracket (140) is in a longitudinal position that does not correspond to when the anvil gap is within a desired operating range (e.g., a green colored region or "green zone"). When the anvil gap is within a desired operating range (e.g., a green colored region or "green zone"), indicator bracket (140) narrows to provide a pair of gaps (145) on either side of an indicator arm (146) that permits lockout feature (82) to pivot, thereby releasing trigger (74). Accordingly, lockout feature (82) and indicator bracket (140) can substantially prevent a user from releasing and operating trigger (74) until anvil (40) is in a predetermined operating range. Of course it should be understood that lockout feature (82) may be omitted entirely in some versions.

This operating range may be visually communicated to the user via an indicator bar (110) of an indicator (104) shown against a scale (130), described briefly above. At the distal end of indicator bracket (140) is a distally projecting indicator arm (146) which terminates at a laterally projecting finger (148) for controlling the movement of indicator (104). Indicator arm (146) and finger (148), best shown in FIG. 5, are configured to engage a tab (106) of indicator (104) such that indicator (104) is pivoted when indicator bracket (140) is actuated longitudinally. In the present example, indicator (104) is pivotably coupled to body (72) at a first end of indicator (104), though this is merely optional and other pivot points for indicator (104) will be apparent to one of ordinary skill in the art in view of the teachings herein. An indicator bar (110) is positioned on the second end of indicator (104) such that indicator bar (110) moves in response to the actuation of indicator bracket (140). Accordingly, as discussed above, indicator bar (110) is displayed through an indicator window (120) against a scale (130) (shown in FIG. 6) to show the relative gap distance d between anvil (40) and stapling head assembly (20).

Of course indicator bracket (140), indicator (104), and/or actuator handle assembly (70) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

II. Exemplary Motorized Circular Stapling Surgical Instrument with Selectable Control In some instances, it may be desirable to provide motorized control of instrument (10). It may further be desirable to enable a user to select between either motorized control or manual control of a motorized version of circular surgical stapling instrument (10). For example, instrument (10) may include an operational mode selection assembly that allows the user to disengage an automated, motorized rotary actuation system and provide manual actuation of that system. It may also be desirable to provide a switch assembly for changing the mode of a single rotary drive between a tissue clamping mode and a tissue cutting/stapling mode. In other words, such a switch assembly may enable a single rotary drive to either actuate anvil (40) clamping features or actuate knife (36) and staple driving features of instrument (10). The examples below include merely illustrative versions of instrument (10) where a single motor can be used to control both clamping and cutting/stapling of tissue via a single rotary drive; where the operator can select between motorized operation and manual operation; and a stapling head cartridge assembly that is responsive to the single rotary drive in motorized and manual operation.

A. Exemplary Operational Mode Selection Assembly

Figure 7:
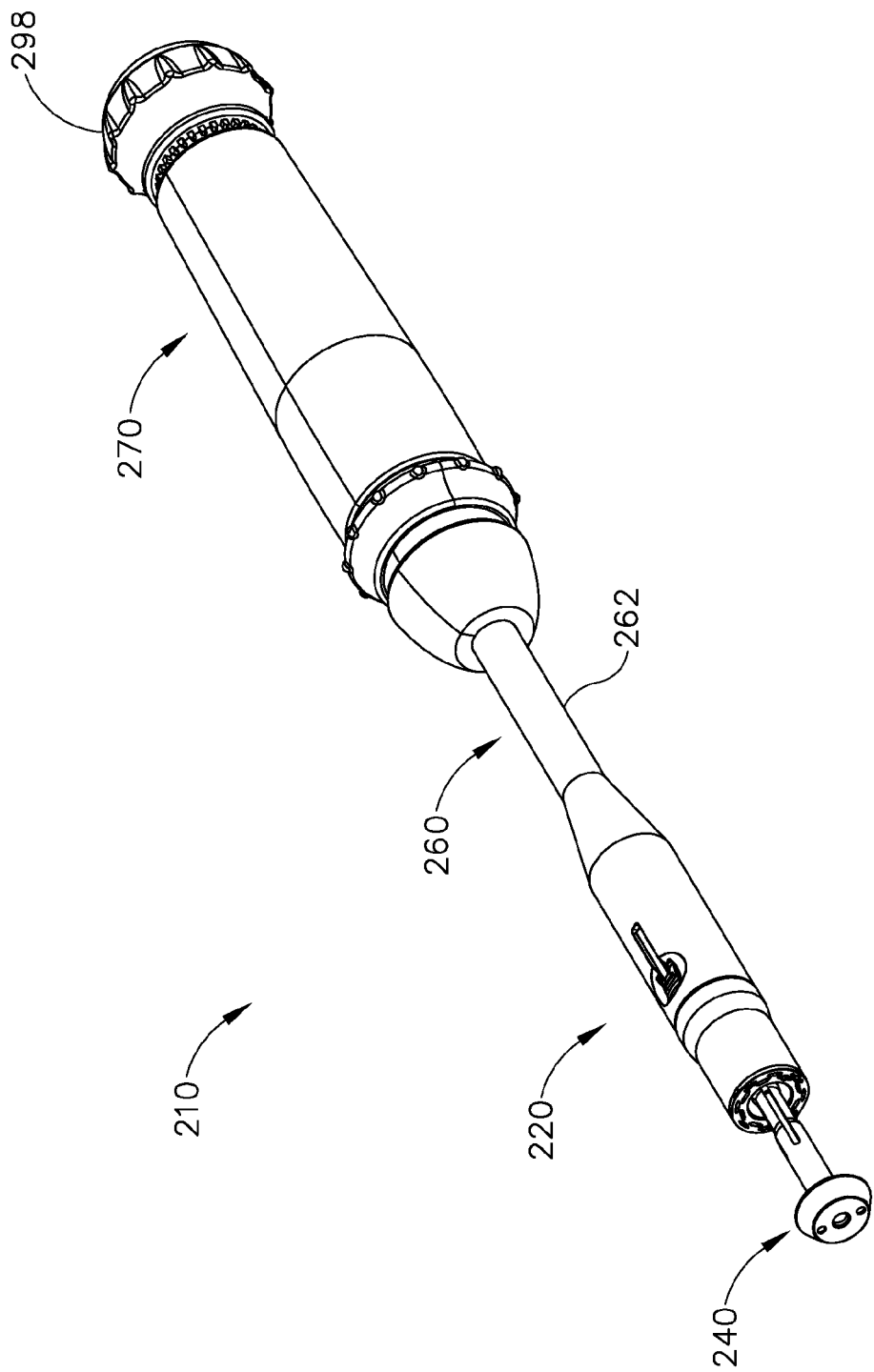
FIG. 7 depicts a perspective view of another exemplary circular stapling surgical instrument.

FIG. 7 shows another exemplary circular stapling instrument (210), which is a selectively motorized variation of instrument (10). Instrument (210) of this example comprises a stapling head assembly (220), an anvil (240), a shaft assembly (260), and a handle assembly (270). Stapling head assembly (220) is similar to stapling head assembly (20) in that stapling head assembly (220) selectively couples with anvil (240). Stapling head assembly (220) is operable to clamp tissue between staple pockets (32) and staple forming pockets (52) of anvil (240). Stapling head assembly (220) comprises a cylindrical knife (36) that is operable to sever tissue captured between stapling head assembly (220) and anvil (240). Stapling head assembly (220) drives staples (66) through the tissue captured between stapling head assembly (220) and anvil (240). Stapling instrument (210) may be used to create a secure anastomosis (e.g., an end-to-end anastomosis) within a gastro-intestinal tract of a patient or elsewhere.

Stapling head assembly (220) differs from stapling head assembly (20) in that stapling head assembly (220) is operable to clamp tissue, sever tissue, and staple tissue all in response to a single rotary input communicated via shaft assembly (260). Accordingly, actuation inputs translated linearly through shaft assembly (260) are not required for stapling head assembly (220), though stapling head assembly (220) may comprise a translating clutch feature. By way of example only, at least part of stapling head assembly (220) may be configured in accordance with at least some of the teachings of U.S. Patent App. No. 13/716,318, entitled "Motor Driven Rotary Input Circular Stapler with Modular End Effector," filed on Dec. 17, 2012, and published as U.S. Pat. Pub. No. 2014/0166728 on Jun. 19, 2014, the disclosure of which is incorporated by reference herein. Other suitable configurations for stapling head assembly (220) will be apparent to those of ordinary skill in the art in view of the teachings herein.

Shaft assembly (260) is similar to shaft assembly (60) in that shaft assembly (260) couples handle assembly (270) with stapling head assembly (220). Shaft assembly (260) differs from shaft assembly (60) in that shaft assembly (260) comprises a single actuation feature, rotary driver actuator (264) shown in FIG. 8. Driver actuator (264) is operable to drive stapling head assembly (220) to clamp tissue, sever tissue, and staple tissue. Accordingly, linear actuation through shaft assembly (260) is not required, though rotary driver actuator (264) may translate longitudinally to shift between a tissue clamping mode and a tissue cutting/stapling mode. For instance, driver actuator (264) may translate from a first longitudinal position, in which rotation of driver actuator (264) provides clamping of tissue at stapling head assembly (220), to a second longitudinal position, in which rotation of driver actuator (264) provides cutting and stapling of tissue at stapling head assembly (220). Some versions of shaft assembly (260) may include one or more flexible sections. An example of a shaft assembly that is configured with flexible sections and that may be incorporated into shaft assembly (260) is disclosed in U.S. Patent App. No. 13/716,323, entitled "Motor Driven Rotary Input Circular Stapler with Lockable Flexible Shaft," filed on Dec. 17, 2012, and published as U.S. Pat. Pub. No. 2014/0166718 on Jun. 19, 2014, the disclosure of which is incorporated by reference herein. Alternatively, shaft assembly (260) may be rigid along the length of shaft assembly (260) or have one or more flexible sections configured in some other fashion.

Figure 8:
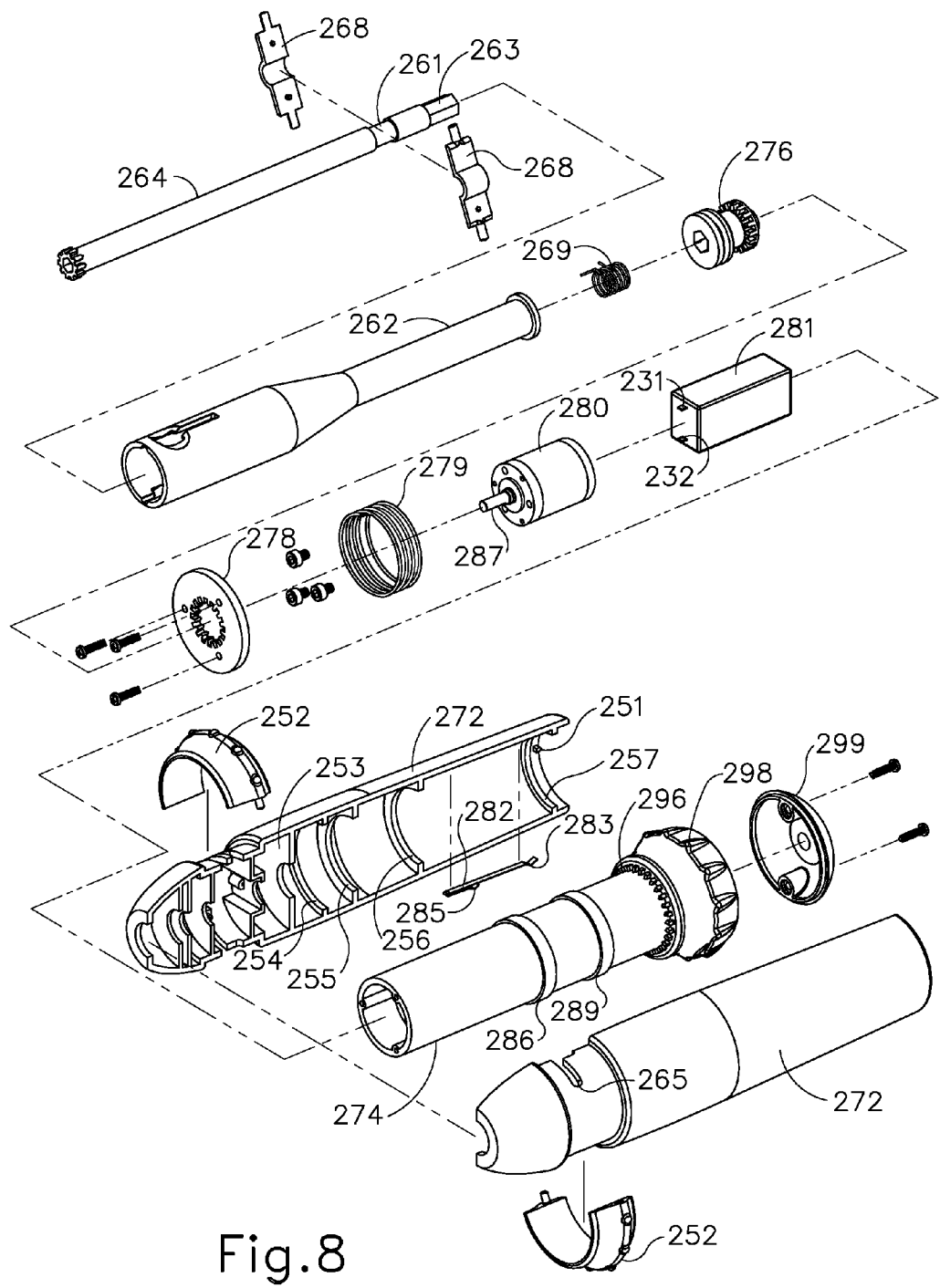
FIG. 8 depicts an exploded view of the handle and shaft assemblies of the instrument of FIG. 7.
Figure 11A:
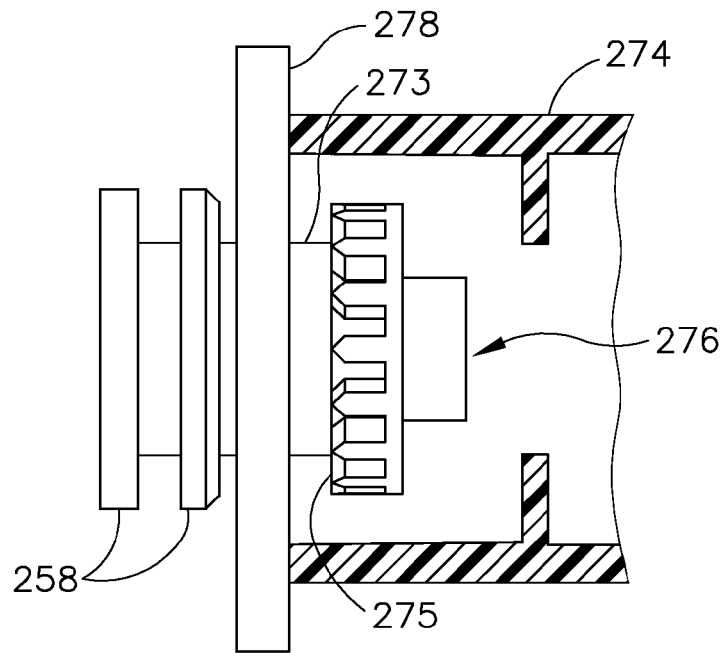
FIG. 11A depicts a side elevational view of an operational mode selection assembly of the instrument of FIG. 7, with a first gear disengaged from a second gear.
Figure 11B:
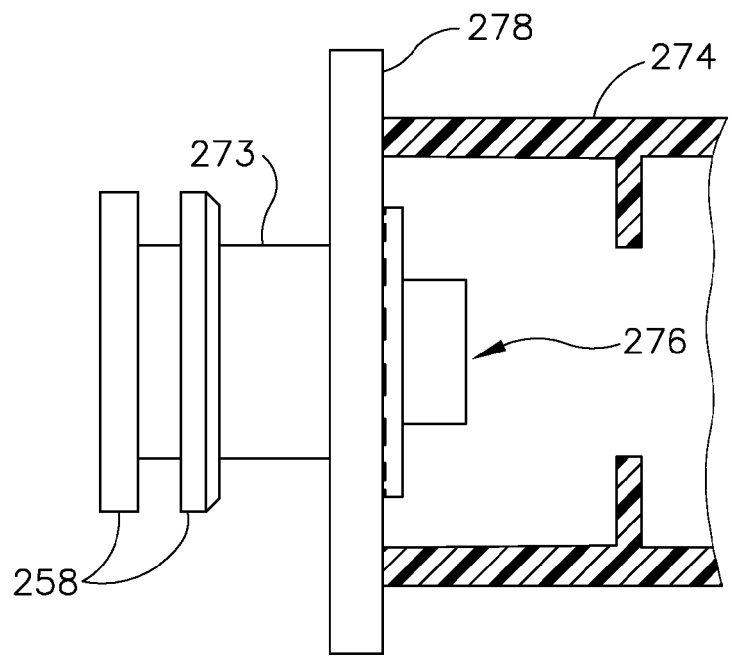
FIG. 11B depicts a side elevational view of the operational mode selection assembly of FIG. 11A, with the first gear engaged with the second gear.

Handle assembly (270) is shown in FIGS. 8-10. Handle assembly (270) comprises a handle housing (272), a motor housing (274), a motor (280), a battery (281), a rotation knob (298), an operational mode selection assembly (which is shown in FIGS. 11A-11B), and a firing ring (252). Motor housing (274) is positioned within handle housing (272). Handle housing (272) comprises ribs (255, 256, 257) extending inwardly into handle housing (272) to support motor housing (274), as shown in FIG. 9. Battery (281) is positioned proximal to motor (280) within motor housing (274). Battery (281) may be removed from motor housing (274) to be replaced, discarded, or recharged. As best seen in FIG. 10, battery (281) comprises electrical contacts (231, 232) extending distally from battery (281). Motor (280) comprises electrical contacts (233, 234) extending proximally from motor (280). Battery electrical contact (232) and motor electrical contact (234) are coupled via conductive metal band (242). Screw (243) couples band (242) to motor housing (274) to fix the position of band (242) relative to motor housing (274). Accordingly, band (242) is configured to constantly couple battery electrical contact (232) and motor electrical contact (234).

As shown in FIG. 10, battery electrical contact (231) is coupled to a conductive metal band (245). Metal band (245) is secured to motor housing (274) via a conductive screw (247). Motor electrical contact (233) is coupled to a conductive metal band (244). Metal band (244) is secured to motor housing (274) via a conductive screw (246). Motor housing (274) is formed of an electrically insulative material (e.g., plastic) and comprises annular contacts (284, 286) wrapped around motor housing (274). Screws (246, 247) are each coupled with a respective annular contact (284, 286) to electrically couple battery electrical contact (231) and motor electrical contact (233) to annular contacts (284, 286), respectively.

Another conductive metal band (282) is secured to handle housing (272). Each end of metal band (282) forms a respective spring contact (283, 285). Motor housing (274) translates proximally and/or distally relative to handle housing (272) to selectively couple and/or decouple spring contacts (283, 285) with annular contacts (284, 286). In particular, when motor housing (274) is in a distal position (FIG. 15A), spring contact (283) engages annular contact (284) and spring contact (285) engages annular contact (286) to couple battery (281) with motor (280) and supply power to motor (280). It should be understood that, since spring contacts (283, 285) are part of the same conductive metal band (282), and since contacts (232, 234) are already coupled via band (242), the engagement between spring contacts (283, 285) and annular contacts (284, 286) completes a circuit between battery (281) and motor (280). This positioning is used to provide motorized actuation of stapling head assembly (220) as will be described in greater detail below. When motor housing (274) is in a proximal position (FIG. 17A), spring contacts (283, 285) are decoupled from annular contacts (284, 286), such that battery (281) is decoupled from motor (280) and motor (280) does not receive power. This positioning is used to provide manual actuation of stapling head assembly (220) as will be described in greater detail below. The annular shape of annular contacts (284, 286) enables proper contact between spring contacts (283, 285) and annular contacts (284, 286) regardless of the angular position of motor housing (274) within handle housing (272). In some versions, band (282) may include a break that is coupled with an external switch, such that a user may actuate the external switch in order to complete the coupling between battery (281) and motor (280) after motor housing (274) is in the distal position.

A proximal end of motor housing (274) is fixedly secured to rotation knob (298), as shown in FIG. 8. Rotation knob (298) protrudes proximally from handle housing (272) and comprises splines (296) extending distally from rotation knob (298). Handle housing (272) comprises corresponding teeth (251) to selectively engage splines (296). Rotation knob (298) is pulled and/or pushed to translate motor housing (274) within handle housing (272). When rotation knob (298) is in a proximal position (FIG. 17A), splines (296) are disengaged from handle housing (272) such that rotation knob (298) and motor housing (274) are free to rotate relative to handle housing (272). This positioning is used to provide manual actuation of stapling head assembly (220) as will be described in greater detail below. When rotation knob (298) is in a distal position (FIG. 15A), splines (296) engage corresponding teeth (251) in handle housing (272) to lock rotation knob (298) and motor housing (274) from rotating relative to handle housing (272). Splines (296) and teeth (251) thus provide a mechanical ground for motor housing (274) relative to handle housing (272). This positioning is used to provide motorized actuation of stapling head assembly (220) as will be described in greater detail below. Rotation knob (298) is biased to the distal position by a resilient member (279) in handle housing (272). In particular, resilient member (279) extends distally from rib (255) of handle housing (272) to a first gear (278), which is unitarily secured to the distal end of motor housing (274). When rotation knob (298) is in the proximal position, resilient member (279) compresses between first gear (278) and rib (255) to resiliently bias handle housing (272) to the distal position.

Figure 12:
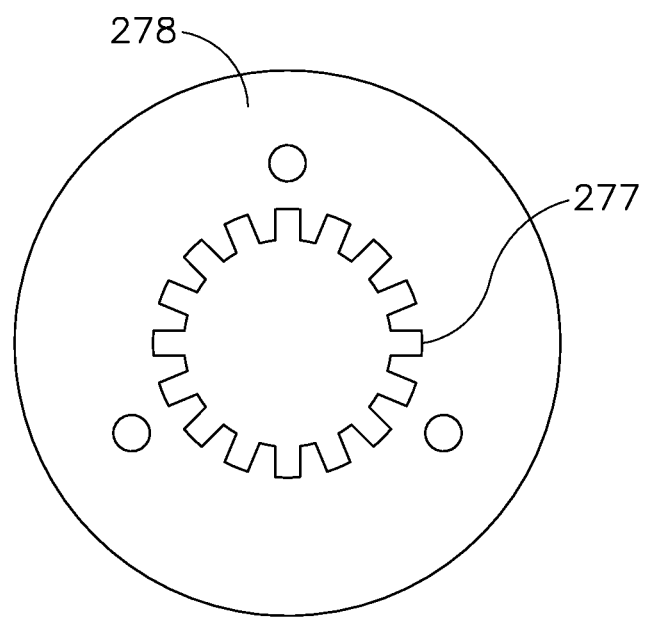
FIG. 12 depicts a front elevational view of the first gear of the operational mode selection assembly of FIG. 11A.
Figure 13:
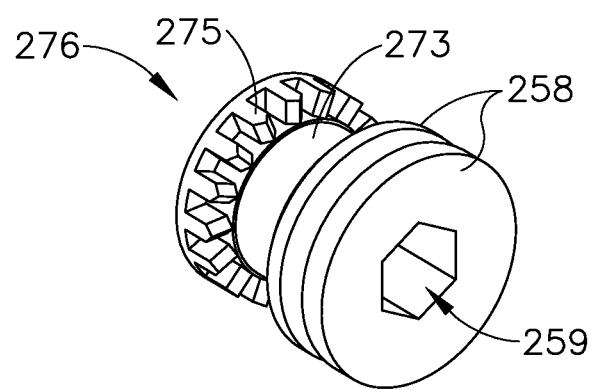
FIG. 13 depicts a perspective view of the second gear of the operational mode selection assembly of FIG. 11A.

An operational mode selection assembly is positioned distal to motor housing (274) within handle housing (272). As shown in FIGS. 11-13, the operational mode selection assembly comprises a first gear (278) and a second gear (276), with first gear (278) being coaxially and slidably disposed about second gear (276). First gear (278) comprises square teeth (277) aligned around an inner opening of first gear (278), as shown in FIG. 12. Teeth (277) define a circumferentially spaced array of recesses. Second gear (276) comprises a shaft (273), splines (275), and annular flanges (258), as shown in FIG. 13. Shaft (273) has a distally presented opening (259). Distally presented opening (259) is hexagonal to receive proximal end (263) of driver actuator (264), which is also hexagonal (FIG. 8). Shaft (273) also has a proximally presented opening (not shown) that is semi-circular to complement and receive drive shaft (287) extending distally from motor (280). Other suitable shapes and configurations of shafts (263, 287) may used to couple second gear (276) with shafts (263, 287).

Splines (275) of second gear (276) are positioned on a proximal end of shaft (273) and extend distally. Splines (275) correspond to teeth (277) of first gear (278), such that splines (275) are configured to fit within the recesses defined between teeth (277). A pair of annular flanges (258) are positioned at a distal end of shaft (273) and extend outwardly to engage an inwardly extending annular rib (253) of handle housing (272), thereby fixing the longitudinal position of second gear (276) within handle housing (272). While annular rib (253) fixes the longitudinal position of second gear (276) within handle housing (272), annular rib (253) nevertheless allows second gear (276) to rotate relative to handle housing (272). Other suitable engagement features to longitudinally fix second gear (276) will be apparent to one with ordinary skill in the art based on the teachings herein.

Figure 17A:
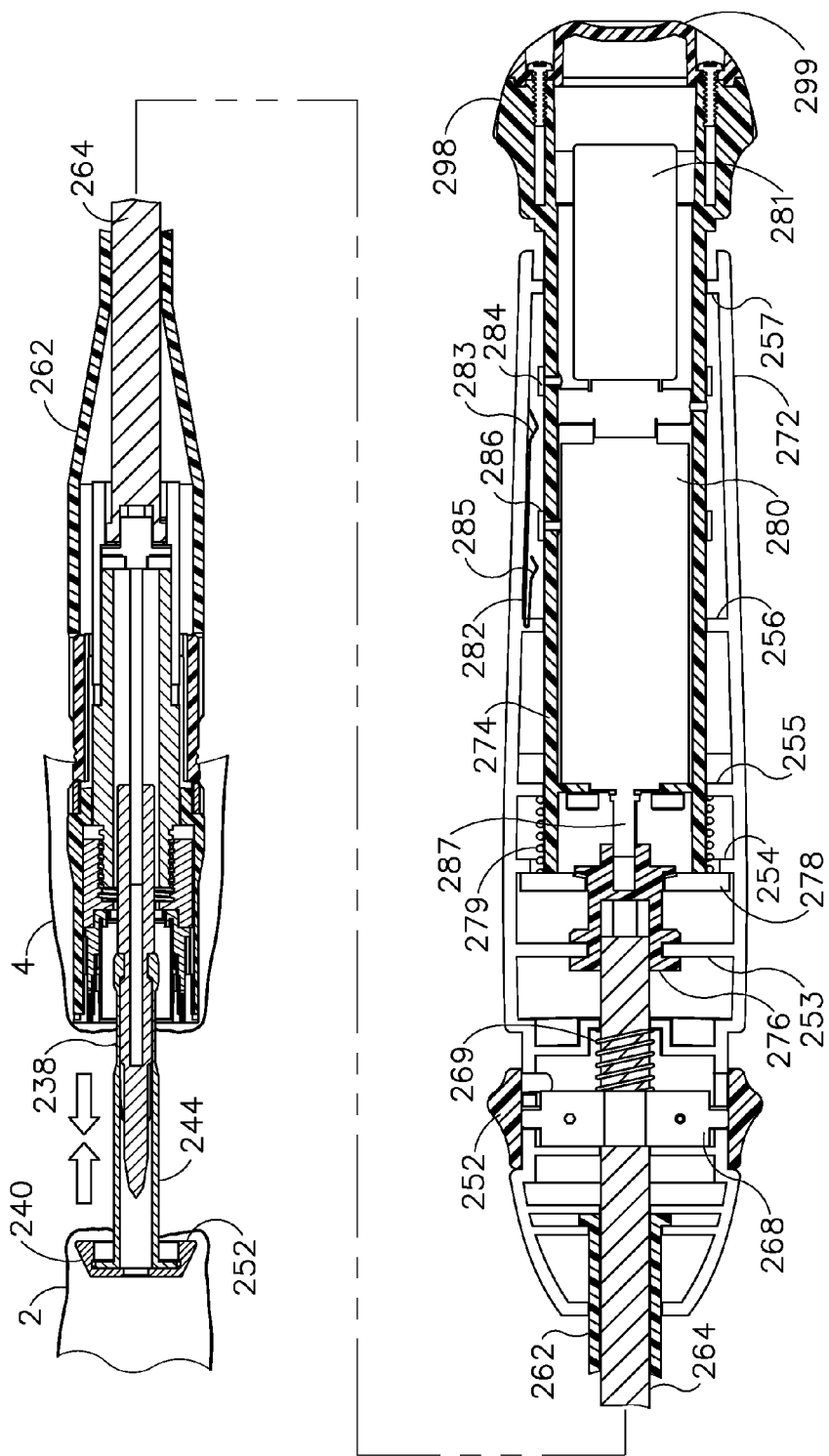
FIG. 17A depicts a cross sectional view of the instrument of FIG. 7, with a manual operational mode selected, showing an anvil being coupled to a trocar.

First gear (278) is positioned around second gear (276), as shown in FIGS. 11A-11B. First gear (278) is fixedly coupled to a distal end of motor housing (274) such that first gear (278) translates and rotates unitarily with motor housing (274). When motor housing (274) is in a proximal position, as shown in FIGS. 11B and 17A, motor (280) and first gear (278) are also in a proximal position. In this position, drive shaft (287) of motor (280) is disengaged from second gear (276) and teeth (277) of first gear (278) engage splines (275) of second gear (276). Thus, when rotation knob (298) rotates, motor housing (274) and first gear (278) also rotate. This positioning thereby provides manual actuation of stapling head assembly (220), as will be described in greater detail below. With teeth (277) of first gear (278) engaged with splines (275), rotation knob (298) thereby rotates second gear (276) relative to motor housing (274). When motor housing (274) is in a distal position, as shown in FIGS. 11A and 15B, motor (280) and first gear (278) are also in a distal position. Motor (280) is engaged with second gear (276) via shafts (287, 273). First gear (278) slides over shaft (273) of second gear (276) to disengage splines (275). Thus, the rotation of drive shaft (287) of motor (280) thereby rotates second gear (276). This positioning thereby provides motorized actuation of stapling head assembly (220), as will be described in greater detail below. In other words, when knob (298) and motor housing (274) are in a distal position as shown in FIGS. 11A and 15B, motor (280) rotates second gear (276). When knob (298) and motor housing (274) are in a proximal position as shown in FIGS. 11B and 17A, knob (298) rotates second gear (276).

Figure 14:
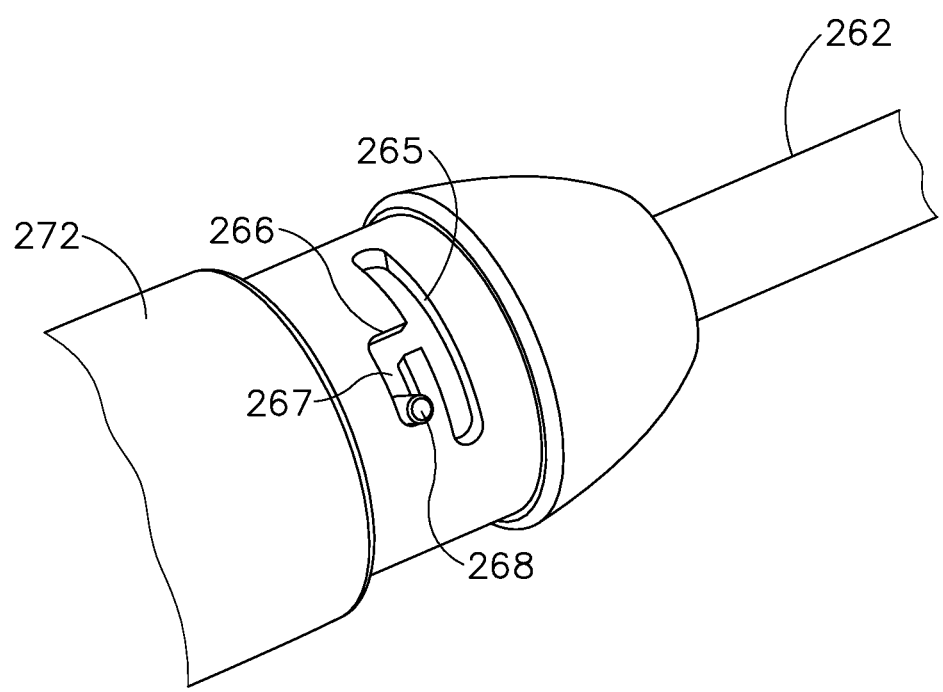
FIG. 14 depicts an enlarged, partial perspective view of the handle assembly of the instrument of FIG. 7.

Referring back to FIGS. 8-9, a distal end of second gear (276) is coupled to driver actuator (264), such that rotation of second gear (276) rotates driver actuator (264). Driver actuator (264) is similar to driver actuator (64). Accordingly, when second gear (276) is rotated, driver actuator (264) is rotated to adjust the gap distance d between anvil (240) and stapling head assembly (220). Handle housing (272) further comprises firing ring (252) and coupling member (268). Coupling member (268) is secured around recess (261) of driver actuator (264), as shown in FIG. 8. Accordingly, coupling member (268) translates with driver actuator (264), but driver actuator (264) is free to rotate within coupling member (268). Coupling member (268) comprises protrusions extending outwardly that connect coupling member (268) to firing ring (252). The protrusions of coupling member (268) extend through slots (265, 266, 267) of housing assembly (272), as shown in FIG. 14. Slot (265) extends circumferentially about part of handle assembly (272). Slot (266) extends proximally from slot (265). Slot (267) extends transversely from slot (266) and is substantially parallel with slot (265). Firing ring (252) is wrapped around handle housing (272) and is rotatable and translatable relative to handle housing (272) to manually drive the protrusions of coupling member (268) through slots (265, 266, 267).

When firing ring (252) is in a distal position, protrusions of coupling member (268) are positioned within slot (265) of handle housing (272). When coupling member (268) is positioned within slot (265), coupling member (268) couples driver actuator (264) with features in stapling head assembly (220) operable to adjust the gap distance d between anvil (240) and stapling head assembly (220). For instance, if coupling member (268) is rotated clockwise within slot (265), the gap distance d is decreased to close anvil (240) relative to stapling head assembly (220). If coupling member (268) is rotated counterclockwise within slot (265), the gap distance d is increased to open anvil (240) relative to stapling head assembly (220). A resilient member (269) is positioned proximal to coupling member (268) to bias coupling member (268) distally (FIG. 8). Coupling member (268) of firing ring (252) may then be translated proximally through slot (266) to slot (267). When firing ring (252) is in the proximal position, protrusions of coupling member (268) are positioned within slot (267). When coupling member (268) is positioned within slot (267), coupling member (268) couples driver actuator (264) with features in stapling head assembly (220) that drive knife (36) and staples (66) in response to rotation of driver actuator (264). For instance, if coupling member (268) is rotated clockwise within slot (267), stapling head assembly (220) drives knife (36) and staples (66). The configuration of slot (367) prevents coupling member (268) from being rotated counterclockwise. Other suitable coupling member (268) rotation configurations will be apparent to one with ordinary skill in view of the teachings herein.

As shown in FIG. 9, a switch (248) is positioned in handle housing (272) to align with coupling member (268). When the motorized operational mode is selected, switch (248) is configured to electrically couple motor (280) and battery (281) when switch (248) is depressed, and switch (248) is configured to electrically decouple motor (280) and battery (281) when switch (248) is not depressed. Coupling member (268) is configured to engage and depress switch (248) when coupling member (268) is rotated. For instance, when coupling member (268) is in a neutral position (e.g., when coupling members (268) are aligned with respective slots (266)), switch (248) is not depressed and motor (280) is decoupled from battery (281). When coupling member (268) is rotated away from the neutral position, coupling member (268) engages switch (248) to depress switch (248) and couple motor (280) with battery (281) to operate instrument (210). It should be understood that housing (272) may include three switches (248). For instance, one switch (248) may be positioned for activation when firing ring (252) is rotated clockwise while in the proximal position (e.g., with coupling member (268) in slot (267)); with another switch (248) being positioned for activation when firing ring (252) is rotated clockwise while in the distal position (e.g., with coupling member (268) in slot (265)); with yet another switch (248) being positioned for activation when firing ring (252) is rotated counterclockwise while in the distal position. A control logic may be in communication with the switches (248) that are activated when firing ring (252) is rotated while in the distal position. Such a control logic may be operable to selectively reverse the direction of rotation by motor (280), to thereby provide selective advancement or retraction of trocar (238) and anvil (240) to adjust the gap distance d, depending on the direction in which firing ring (252) is rotated.

It should be understood that firing ring (252) and coupling member (268) act as a clutch control to shift driver actuator (264) from an anvil clamping mode (when coupling member (268) is in the distal position) to a cutting/stapling mode (when coupling member (268) is in the proximal position). An example of a stapling head assembly (220) responsive to such changes in driver actuator (264) positioning is disclosed in U.S. Patent App. No. 13/716,318 , entitled "Motor Driven Rotary Input Circular Stapler with Modular End Effector," filed on on, Dec. 17, 2012, and published as U.S. Pat. Pub. No. 2014/0166728 on Jun. 19, 2014, the disclosure of which is incorporated by reference herein. Other suitable forms that stapling head assembly (220) may take will be apparent to those of ordinary skill in the art in view of the teachings herein. Outer tubular member (262) is coupled to actuator handle assembly (270). Outer tubular member (262) is similar to outer tubular member (62) to provide a mechanical ground between stapling head assembly (220) and handle assembly (270).

1. Motorized Operation

Figure 15A:
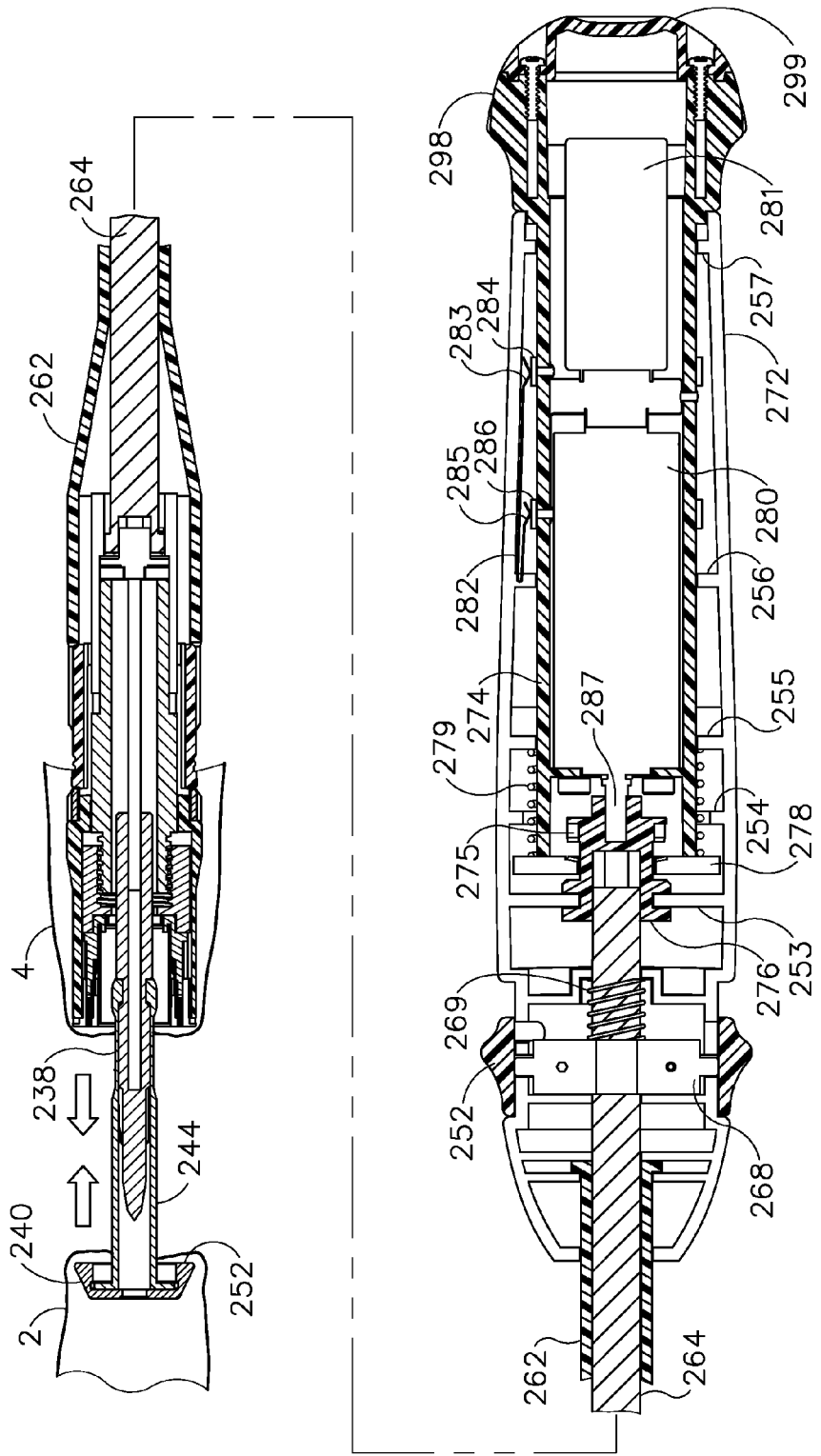
FIG. 15A depicts a cross sectional view of the instrument of FIG. 7, with a motorized operational mode selected, showing an anvil being coupled to a trocar.
Figure 15B:
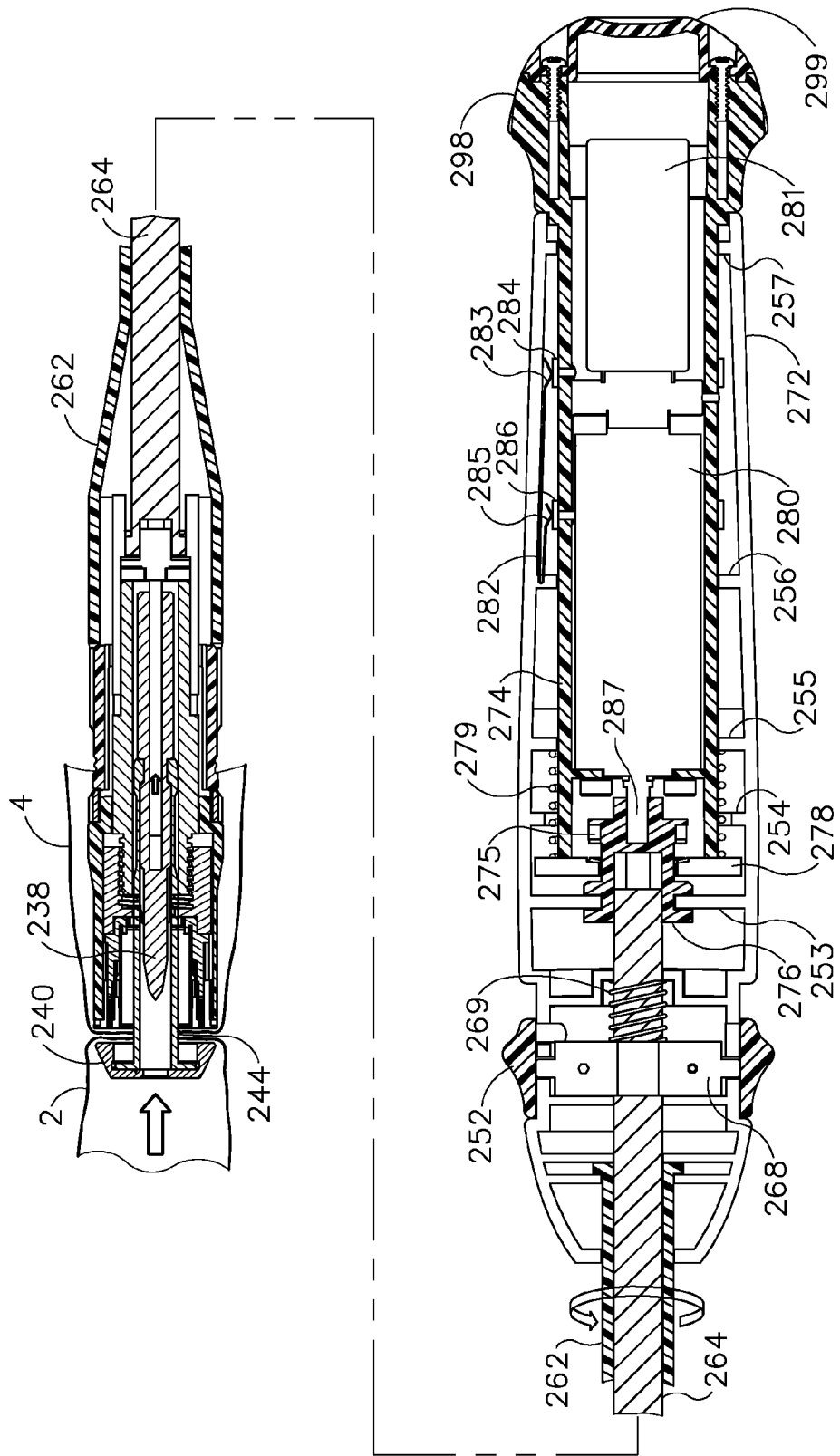
FIG. 15B depicts a cross sectional view of the instrument of FIG. 7, with a motorized operational mode selected, in a tissue clamping position.
Figure 15C:
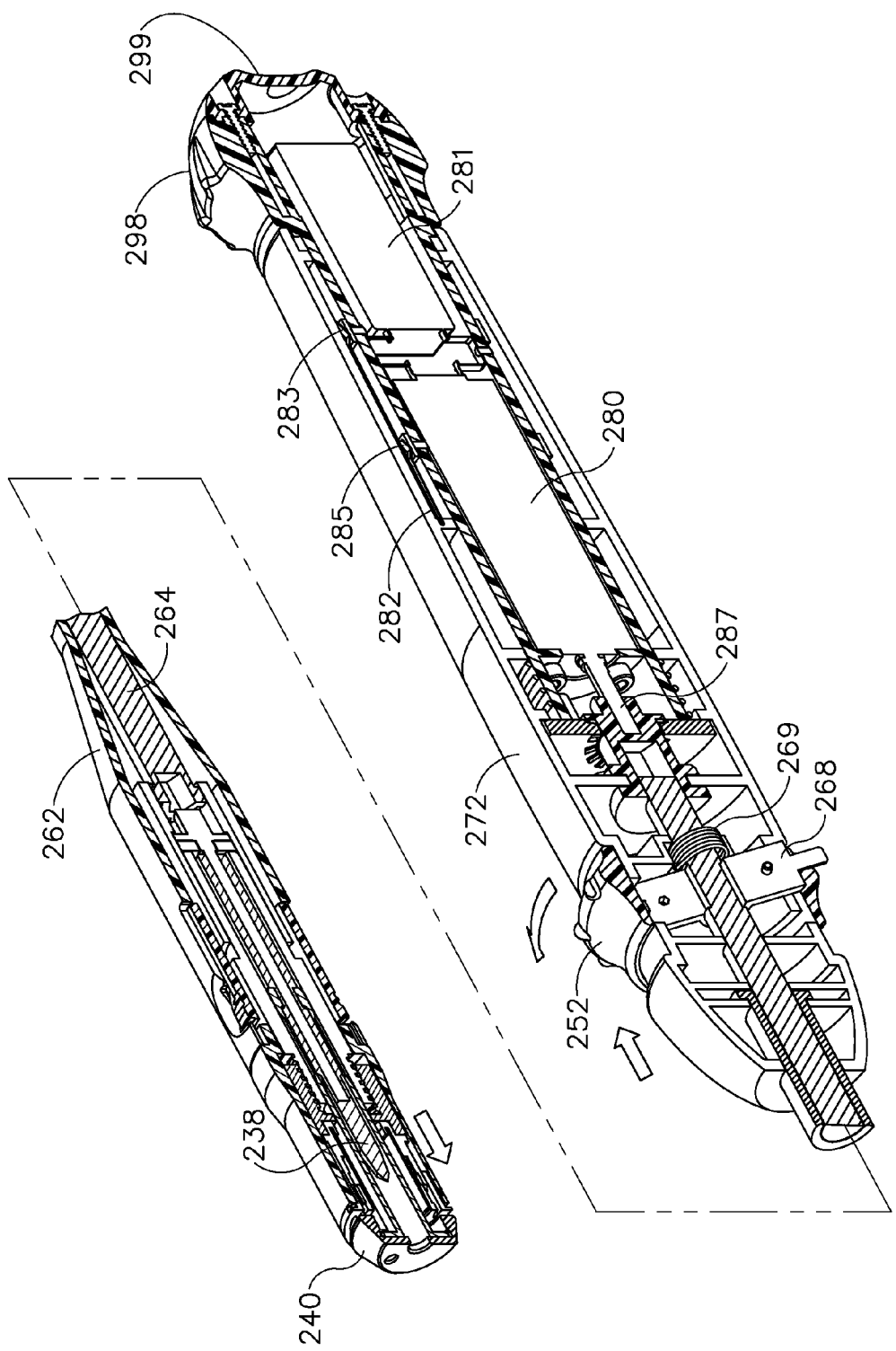
FIG. 15C depicts a cross sectional view of the instrument of FIG. 7, with a motorized operational mode selected, in a fired position.

FIGS. 15A-15C show instrument (210) during motorized operation. FIG. 15A shows anvil (240) being coupled to trocar (238). Anvil (240) couples with trocar (238) in a manner similar to that described above with respect to anvil (40) and trocar (38). When motorized operation is selected, rotation knob (298) is in a distal position. In the distal position, splines (296) of rotation knob (298) engage corresponding teeth (251) in handle housing (272) to lock rotation knob (298) from rotating relative to handle housing (272). When rotation knob (298) is in the distal position, motor housing (274) is also in a distal position. When motor housing (274) is in the distal position, spring contacts (283, 285) are aligned with annular contacts (284, 286) to couple electrical contact (231) of battery (281) with electrical contact (233) of motor (280). Power is supplied from battery (281) to motor (280) when coupling member (268) is rotated to depress switch (248). Motor (280) is engaged with second gear (276) via shafts (287, 273) and first gear (278) is disengaged from splines (275), thereby permitting second gear (276) to rotate relative to first gear (278), motor housing (274), and handle housing (272). Protrusions of coupling member (268) are positioned distally within slot (265) of handle housing (272) to lock the longitudinal position of firing ring (252) and driver actuator (264).

As shown in FIG. 15B, firing ring (252) is rotated clockwise to translate coupling member (268) within slot (267). As coupling member (268) is rotated, switch (248) is depressed to couple motor (280) and battery (281) and supply power to motor (280). Motor (280) is thus activated to rotate shaft (287). Shaft (287) thereby rotates second gear (276). Because second gear (276) is coupled to driver actuator (264), the rotation of second gear (276) also rotates driver actuator (264). This rotation of driver actuator (264) drives features in stapling head assembly (220) to adjust the gap distance d between anvil (240) and stapling head assembly (220). Once anvil (240) is in a desired position relative to stapling head assembly (220), firing ring (252) is rotated counterclockwise to a neutral position to release switch (248) such that motor (280) is decoupled from battery (281). Instrument (210) may then be fired, as shown in FIG. 15C. Firing ring (252) is translated to position coupling member (268) out of slot (265) to the proximal position in slot (267). When coupling member (268) is translated proximally to slot (267), coupling member (268) also translates driver actuator (264) proximally to couple driver actuator (264) with features in stapling head assembly (220) operable to drive knife (36) distally and to drive staples (66) into anvil (240) to staple the clamped tissue (2, 4) to create an anastomosis. Firing ring (252) is rotated clockwise within slot (267) to depress switch (248) to again couple battery (281) with motor (280) to supply power to motor (280). Motor (280) is again rotated with coupling member (268) and driver actuator (264) in the proximal position. This rotation is communicated to driver actuator (264) via drive shaft (287) and second gear (276), and is thereby communicated to driver actuator (264) to cut and staple tissue (2, 4). Firing ring (252) may then be rotated counterclockwise within slot (267) to the neutral position to release switch (248) and decouple motor (280) from battery (281).

2. Selection of Operation Mode

Figure 16:
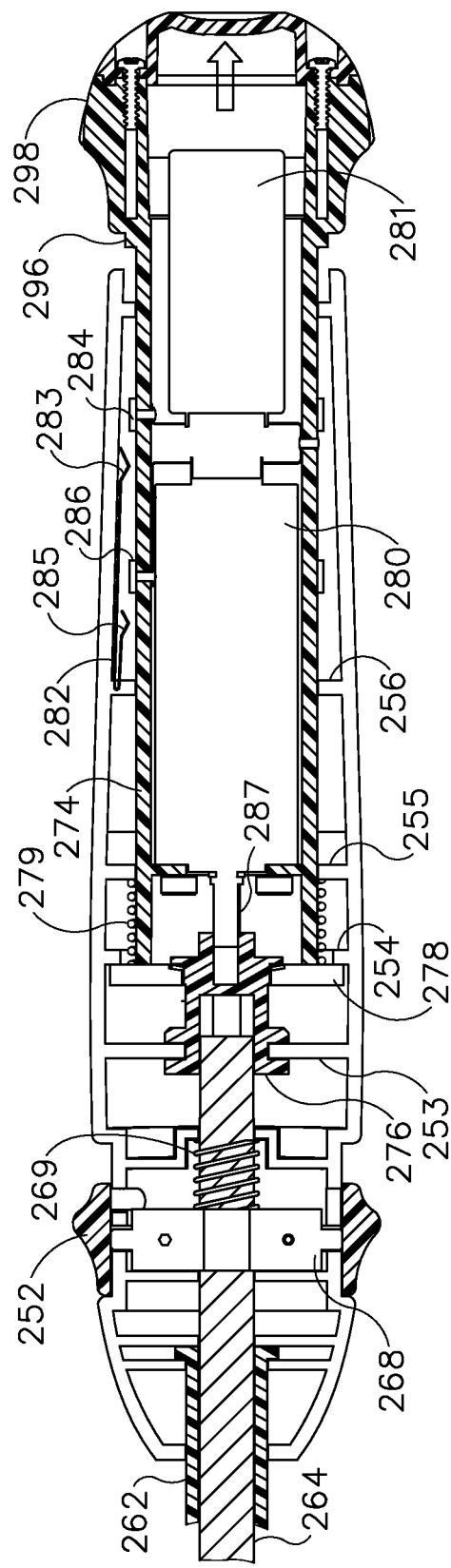
FIG. 16 depicts a cross sectional view of the handle assembly of the instrument of FIG. 7 showing the manual operational mode being selected.

As shown in FIG. 16, instrument (210) is switched from motorized operation to manual operation. A user may grasp rotation knob (298) to translate rotation knob (298) from the distal position to the proximal position. In the proximal position, splines (296) of rotation knob (298) disengage from corresponding teeth (251) in handle housing (272) to allow rotation knob (298) to rotate relative to handle housing (272). This also allows motor housing (274) and first gear (278) to rotate relative to handle housing (272). When rotation knob (298) is in the proximal position, motor housing (274) is also in a proximal position. When motor housing (274) is in the proximal position, spring contacts (283, 285) are offset from annular contacts (284, 286) to decouple battery (281) from motor (280) such that no power is supplied to motor (280). First gear (278) translates proximally to engage splines (275) of second gear (276). Thereby, rotation of rotation knob (298) rotates motor housing (274), first gear (278), second gear (276), and driver actuator (264). A user may also push rotation knob (298) back distally to reselect motorized operation. By using rotation knob (298) as an actuator to select between motorized and manual operation, the need for lockouts or switches to simultaneously remove power to motor (280) is eliminated. Rotation knob (298) thus provides a "bailout" system of motorized operation, while allowing instrument (210) to be fully operational in the manual operational mode. It should therefore be understood that even if an operator initially uses instrument (210) in a motorized mode, the operator may quickly and easily convert instrument (210) to a manually operated mode simply by pulling on rotation knob (298), without sacrificing essential functionality of instrument (210).

3. Manual Operation

Figure 17B:
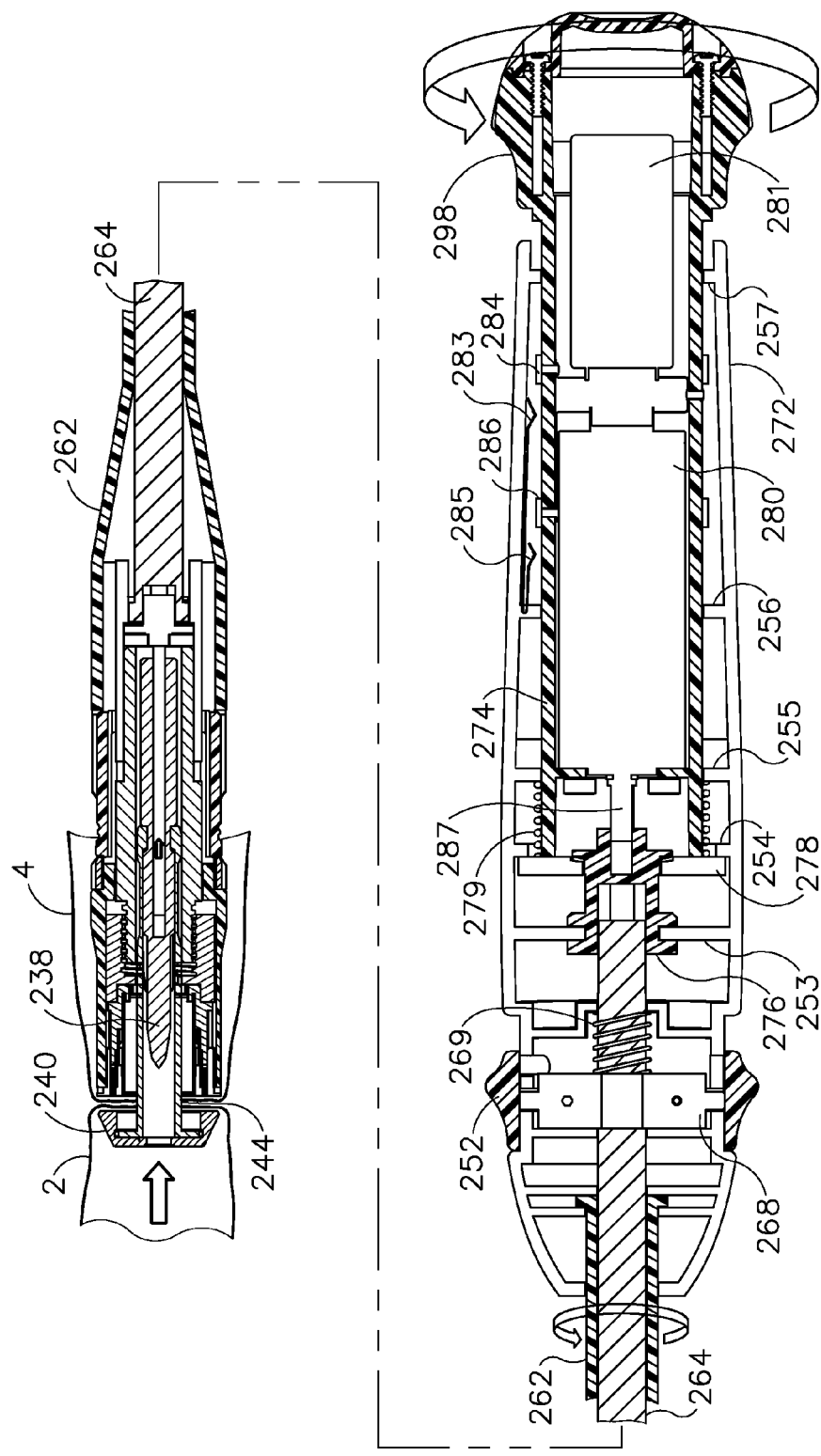
FIG. 17B depicts a cross sectional view of the instrument of FIG. 7, with a manual operational mode selected, in a tissue clamping position.
Figure 17C:
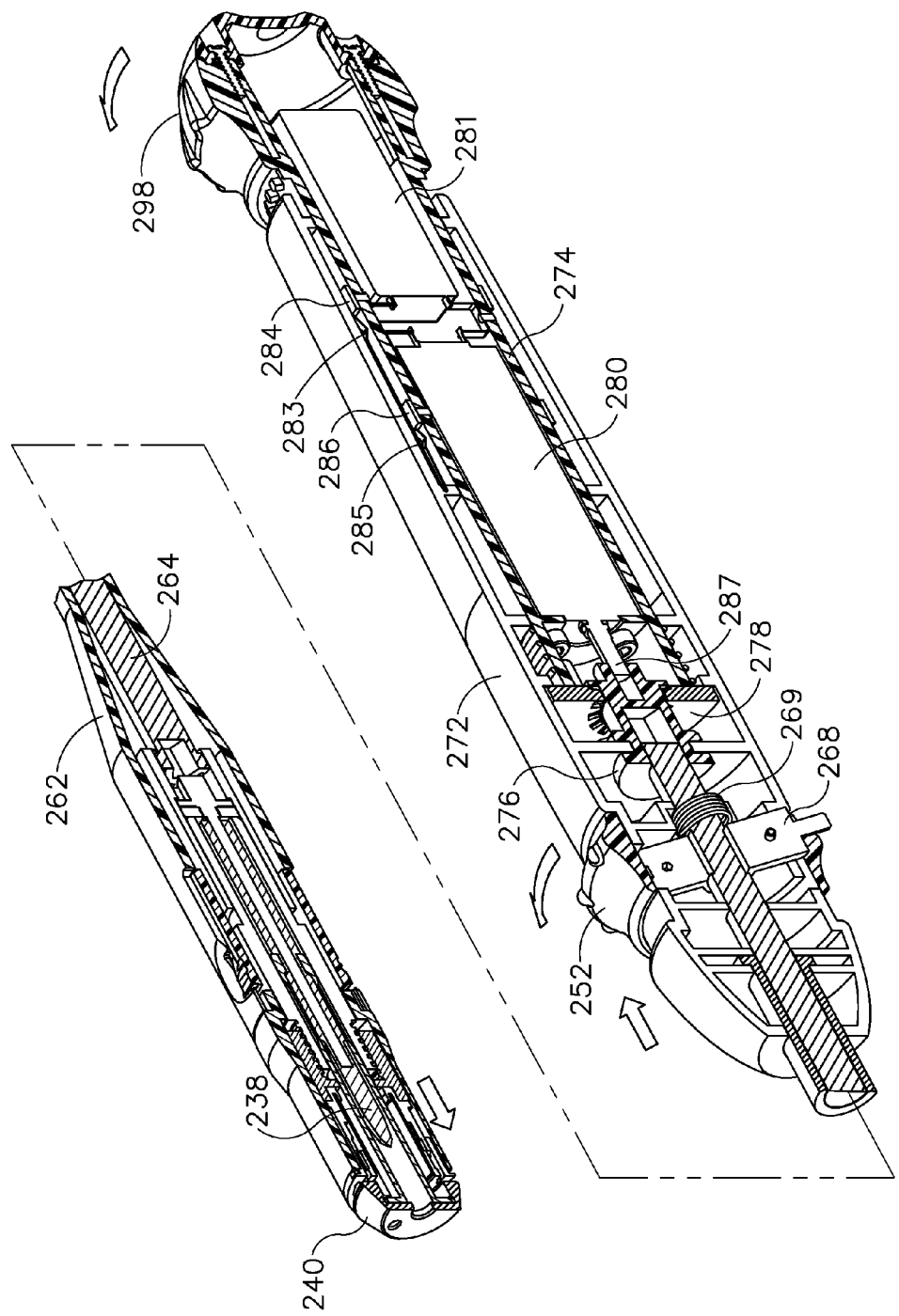
FIG. 17C depicts a cross sectional view of the instrument of FIG. 7, with a manual operational mode selected, in a fired position.

FIGS. 17A-17C show instrument (210) during manual operation. FIG. 17A shows anvil (240) being coupled to trocar (238). Rotation knob (298) is in the proximal position, as described above. As shown in FIG. 17B, rotation knob (298) is rotated to rotate motor housing (274) relative to handle housing (272). Motor housing (274) thereby rotates first gear (278). First gear (278) is engaged with splines (275) to rotate second gear (276). Because second gear (276) is coupled to driver actuator (264), the rotation of second gear (276) also rotates driver actuator (264). This rotation of driver actuator (264) rotates features in stapling head assembly (220) to adjust the gap distance d between anvil (240) and stapling head assembly (220). Once anvil (240) is in a desired position relative to stapling head assembly (220), instrument (210) may be fired, as shown in FIG. 17C. Firing ring (252) is translated from the distal position and out of slot (265) to the proximal position with slot (267). When coupling member (268) is translated proximally to slot (267), coupling member (268) also translates driver actuator (264) proximally to couple driver actuator (264) with features in stapling head assembly (220) operable to drive knife (36) distally and to drive staples (66) into anvil (240) to staple the clamped tissue (2, 4) to create an anastomosis. Rotation knob (298) is again rotated with coupling member (268) and driver actuator (264) in the proximal position. This rotation is communicated to driver actuator (264) via first gear (278) and second gear (276), and is thereby communicated to driver actuator (264) to cut and staple tissue (2, 4).

4. Control Assembly

Figure 18:
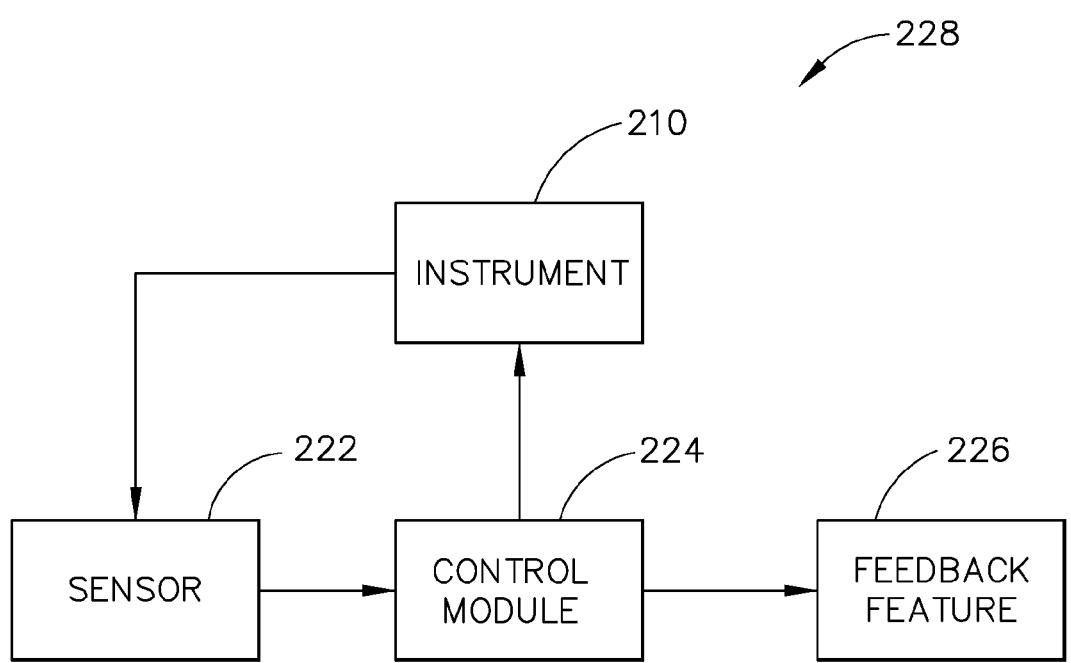
FIG. 18 depicts a schematic of an exemplary control assembly for use with the instrument of FIG. 7.

FIG. 18 shows an exemplary control assembly (228) for use with instrument (210). Control assembly (228) comprises a sensor (222), a control module (224), and a feedback feature (226). Feedback feature (226) may be operable to provide visual, audio, and/or haptic feedback (LED lights, LED display, speaker, vibration generator, etc.). Sensor (222) is coupled to instrument (210) and is configured to detect movement within the drive train of instrument (210). For example, sensor (222) may comprise an encoder positioned to detect rotation of driver actuator (264) or some other rotating component of drive train (e.g., a component that rotates but does not also translate). Sensor (222) is coupled with control module (224) to provide the sensed signal to control module (224). Control module (224) is configured to process the sensed signal and may determine the selected operational mode of instrument (210), the gap distance d between anvil (240) and stapling head assembly (220), and/or the firing of knife (36) and staples (66). In the present example, control module (224) is coupled with instrument (210) and feedback feature (226). However, control module (224) may be coupled with either of instrument (210) or feedback feature (226). Control module (224) may also be coupled with switch (248) to actuate motor (280) when switch (248) is depressed. Each of sensor (222), control module (224), and feedback feature (226) may be located within instrument (210) or remotely from instrument (210).

Based on the sensed signal, control module (224) is operable to actuate instrument (210) and/or feedback feature (226). For example, control module (224) may actuate feedback feature (226) to indicate the selected operational mode of instrument (210). In some versions, feedback feature (226) may have a first LED corresponding to the motorized operational mode and a second LED corresponding to the manual operational mode. Sensor (222) may detect the proximal and/or distal position of rotation knob (298) and/or motor housing (274) and provide the information to control module (224). Control module (224) may then illuminate the first LED if sensor (222) detects the proximal position to indicate the motorized operational mode is selected. Control module (224) may illuminate the second LED if sensor (222) detects the distal position to indicate the manual operational mode is selected. Alternatively, feedback feature (226) may have only one LED which is either illuminated or not to indicate the operational mode, or feedback feature (226) may have a speaker to provide a sound when the operational mode is changed.

In some versions, control module (224) may actuate feedback feature (226) to indicate the selected mode of stapling assembly (220). Feedback feature (226) may have a first LED corresponding to the tissue clamping mode and a second LED corresponding to the firing mode. Sensor (222) may detect the proximal and/or distal position of firing ring (252), coupling member (268) and/or driver actuator (264) and provide the information to control module (224). Control module (224) may then illuminate the first LED if sensor (222) detects the distal position to indicate the tissue clamping mode is selected. Control module (224) may illuminate the second LED if sensor (222) detects the proximal position to indicate the firing mode is selected. Alternatively, feedback feature (226) may have only one LED which is either illuminated or not to indicate stapling head assembly (220) mode, or feedback feature (226) may have a speaker to provide a sound when stapling head assembly (220) mode is changed.

In addition or in the alternative, control module (224) may actuate feedback feature (226) to indicate the gap distance d between anvil (240) and stapling head assembly (220). Sensor (222) may detect the number of rotations of driver actuator (264). Control module (224) may then determine the gap distance d based on the sensed signal and actuate feedback feature (226). Feedback feature (226) may comprise a plurality of LEDs that individually illuminate to indicate the gap distance d. As gap distance d increases, LEDs may illuminate to correspond to the gap distance d. As gap distance d decreases, LEDs may turn off to correspond to the gap distance d. As another merely illustrative example, feedback feature (226) may comprise an LED display screen that provides a real-time indication of the gap distance d. Feedback feature (226) may also have a speaker that emits a sound that changes in either pitch or volume to indicate the corresponding gap distance d. Alternatively, one LED may be used to indicate when a particular gap distance d has been reached, or a sound may be provided when the particular gap distance d has been reached.

In versions where feedback feature (226) includes the capability of providing haptic feedback to the operator, it should be understood that various conventional components may be incorporated into handle assembly (270) to provide such haptic feedback. It should also be understood that haptic feedback may be provided through motor (280). By way of example only, feedback feature (226) may be configured to provide a sine wave signal to motor (280) to essentially rotate drive shaft (287) slightly clockwise and then immediately rotating it slightly counterclockwise the exact same amount. The net result would be zero rotational displacement of drive shaft (287). When this sequence is repeated (e.g., in a rapid succession), the movement of drive shaft (287) may cause handle assembly (270) to vibrate or otherwise shake enough for the operator to feel it through the hand that grasps handle assembly (270). With the zero net movement of drive shaft (287) through this feedback algorithm, the haptic feedback may result in no net actuation of anything in head assembly (220), regardless of whether driver actuator (264) is in the distal position or the proximal position. Such haptic feedback may be provided to indicate the end of a stapling stroke, to indicate a lockout condition, and/or to indicate some other condition. Various other suitable ways in which audio, visual, and/or haptic feedback may be provided will be apparent to those of ordinary skill in the art in view of the teachings herein.

In some versions, control module (224) may actuate instrument (210). Sensor (222) may be configured to detect when knife (36) and staples (66) have been fired. Control module (224) may thus automatically reverse motor (280) once knife (36) and staples (66) have been fired. Control module (224) may also actuate feedback feature (226) to indicate to a user that instrument (210) has been fired. Other suitable ways in which sensors (222), control module (224), and feedback feature (226) may be used will be apparent to those of ordinary skill in the art in view of the teachings herein. It should also be understood that such features may be simply omitted if desired.

B. Exemplary Switch Assembly

Figure 19:
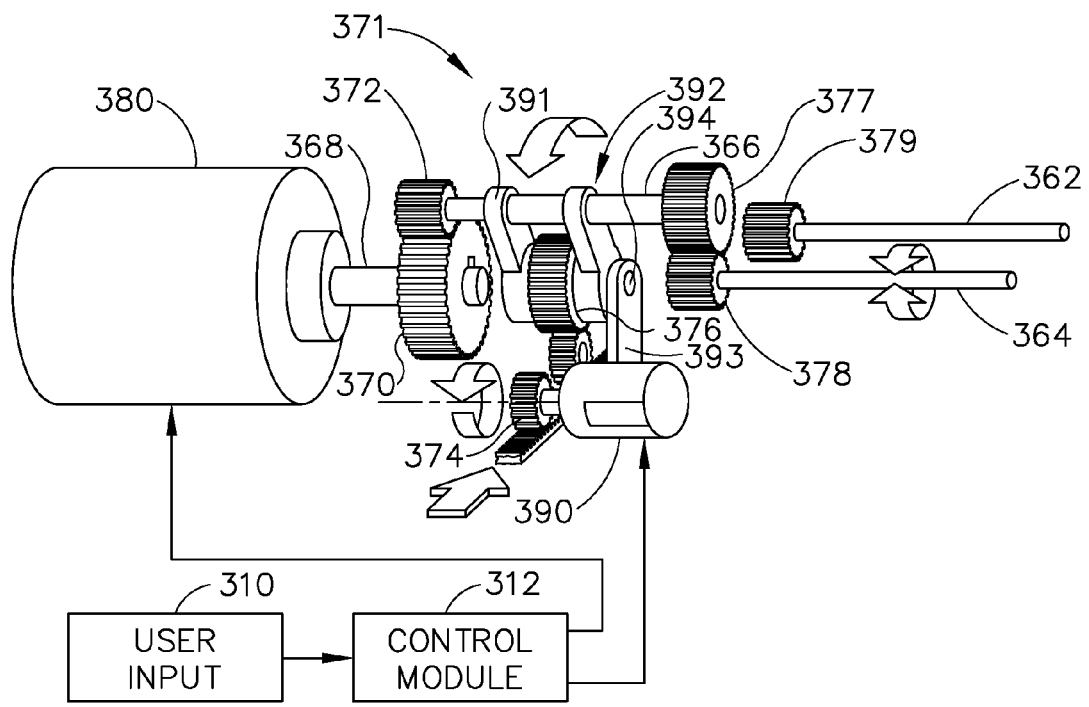
FIG. 19 depicts a partial perspective view of another exemplary operational mode selection assembly.
Figure 20:
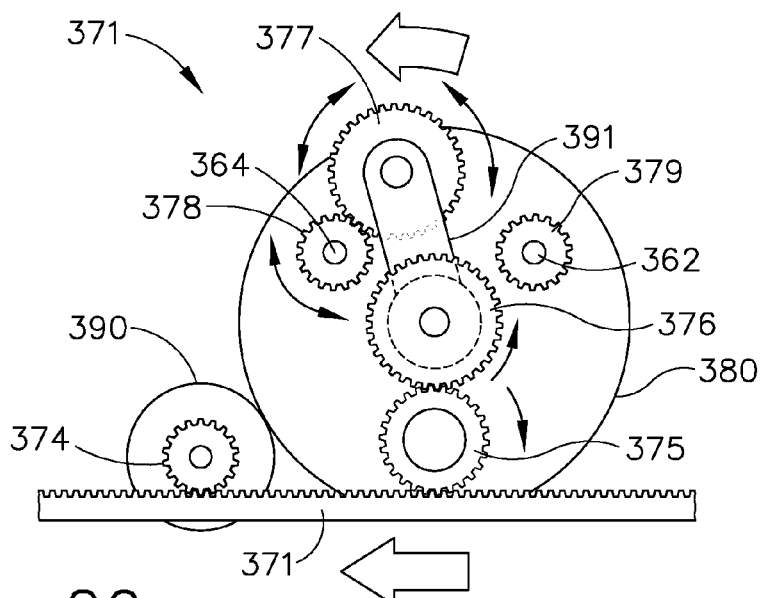
FIG. 20 depicts a front view of the operational mode selection assembly of FIG. 19.

As described above, surgical stapling instrument (10, 210) has two sub-systems, a closure sub-system (to clamp tissue between anvil (40, 240) and stapling head assembly (20, 220)) and a firing sub-system (to drive knife (36) and staples (66) distally toward anvil (40, 240)), in order to create an anastomosis. It may be desirable to power both sub-systems with a single rotary motor to eliminate the cost and packaging of an additional motor and transmission. FIGS. 19-20 show an exemplary drive assembly (371) configured to power two sub-systems with a single rotary motor (380). While instrument (210) provided closure and firing with a single rotary drive shaft, drive assembly (371) of this example provides closure and firing through two separate rotary drive shafts driven by a single motor (380). Drive assembly (371) comprises a motor (380), a transmission shaft (392), a solenoid (390), a closure rod (364), and a firing rod (362). Motor (380) comprises a shaft (368) extending from motor (380) and a gear (370) coupled to shaft (368). Transmission shaft (392) comprises a gear (372) engaged with gear (370) of motor (380). A gear (377) is positioned on the opposing end of transmission shaft (392).

A pivoting swing arm (391) is wrapped around transmission shaft (392) such that transmission shaft (392) may freely rotate relative to swing arm (391), as shown in FIG. 18. Swing arm (391) extends from transmission shaft (392) and comprises a gear (376). Gear (376) is fixedly secured to swing arm (391). A pin (394) extends from swing arm (391) and is coaxial with gear (376). Pin (394) is pivotally supported by a bracket (393), such that swing arm (391) is pivotable about pin (394) relative to bracket (393) in response to rotation of gear (376). Solenoid (390) comprises a gear (374) coupled to a rack (371). Rack (371) is also coupled to a gear (375), which engages gear (376) of swing arm (391). Alternatively, gear (374) of solenoid (390) may directly couple to gear (376) of swing arm (391). Closure rod (364) comprises a gear (378). Firing rod (362) is positioned adjacent to and substantially parallel with closure rod (364). Firing rod (362) comprises a gear (379). Gear (377) of transmission shaft (392) selectively swings to engage either gear (378) of closure rod (364) or gear (379) of firing rod (362).

As shown in FIGS. 19-20, transmission shaft (392) is positioned to engage closure rod (364). Accordingly, when motor (380) is activated, shaft (368) rotates gear (370). Gear (370) thereby rotates gear (372) and transmission shaft (392) to rotate gear (377). Because gear (377) is engaged with gear (378), transmission shaft (392) thereby rotates closure rod (364). Closure rod (364) may be used to adjust the gap distance d between anvil (40, 240) and stapling head assembly (20, 220). If a user desires to switch to the firing sub-system, solenoid (390) may be actuated. When solenoid (390) is actuated, solenoid (390) rotates gear (374) to translate rack (371). Rack (371) then rotates gear (375) and gear (376) of swing arm (391). Gear (376) thereby pivots swing arm (391). As swing arm (391) pivots, swing arm (391) translates transmission shaft (392) such that transmission shaft (392) disengages closure rod (364) and engages firing rod (362). Accordingly, when motor (380) is activated, shaft (368) rotates gear (370). Gear (370) thereby rotates gear (372) and transmission shaft (392) to rotate gear (377). Because gear (377) is now engaged with gear (379), transmission shaft (392) thereby rotates firing rod (362). Firing rod (364) may be used to drive knife (36) and staples (66) distally toward anvil (40, 240). Solenoid (390) may then be actuated again such that switch assembly (371) switches to the closure sub-system via swing arm (391).

Solenoid (390) may be button activated or be otherwise manually activated. Alternatively, switching assembly (371) may incorporate logic such that solenoid (390) is activated automatically. For instance, a user may actuate drive assembly (371) by inputting a user input (310) into a control module (312), as shown in FIG. 19. Control module (312) is coupled to motor (380) and solenoid (390) to selectively actuate motor (380) and/or solenoid (390) based on user input (310). Control module (312) may be integral with instrument (10, 210), or control module (312) may be a separate assembly. Suitable control module (312) configurations will be apparent to one with ordinary skill in the art in view of the teachings herein.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/693,430, entitled "Trans-Oral Circular Anvil Introduction System with Dilation Feature," filed Dec. 4, 2012, now U.S. Pat. Pub. No. 2014/0151429, published Jun. 5, 2014, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/688,951, entitled "Surgical Staple with Integral Pledget for Tip Deflection," filed Nov. 29, 2012, now U.S. Pat. No. 9,289,207, issued Mar. 22, 2016, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/706,827, entitled "Surgical Stapler with Varying Staple Widths Along Different Circumferences," filed Dec. 6, 2012, now U.S. Pat. Pub. No. 2014/0158747, published Jun. 12, 2014, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/688,992, entitled "Pivoting Anvil for Surgical Circular Stapler," filed Nov. 29, 2012, now U.S. Pat. Pub. No. 2014/0144969, published May 29, 2014, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/693,455, entitled "Circular Anvil Introduction System with Alignment Feature," filed Dec. 4, 2012, now U.S. Pat. Pub. No. 2014/0151430, published Jun. 5, 2014, the disclosure of which is incorporated by reference herein. Various suitable ways in which such teachings may be combined will be apparent to those of ordinary skill in the art.

Similarly, at least some of the teachings herein may be readily combined with one or more teachings of U.S. Patent App. No. 13/716,313, entitled "Circular Stapler with Selectable Motorized and Manual Control, Including a Control Ring," filed on Dec. 17, 2012, and published as U.S. Pat. Pub. No. 2014/0166717, the disclosure of which is incorporated by reference herein. Various suitable ways in which such teachings may be combined will be apparent to those of ordinary skill in the art.

Similarly, at least some of the teachings herein may be readily combined with one or more teachings of U.S. Patent App. No. 13/716,318, entitled "Motor Driven Rotary Input Circular Stapler with Modular End Effector," filed on Dec. 17, 2012, and published as U.S. Pat. Pub. No. 2014/0166728 on Jun. 19, 2014, the disclosure of which is incorporated by reference herein. Various suitable ways in which such teachings may be combined will be apparent to those of ordinary skill in the art.

Similarly, at least some of the teachings herein may be readily combined with one or more teachings of U.S. Patent App. No. 13/716,323, entitled "Motor Driven Rotary Input Circular Stapler with Lockable Flexible Shaft," filed on Dec. 17, 2012 and published as U.S. Pat. Pub. No. 2014/0166718 on Jun. 19, 2014, the disclosure of which is incorporated by reference herein. Various suitable ways in which such teachings may be combined will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for stapling tissue, the apparatus comprising:
   (a) a stapling head assembly, wherein the stapling head assembly is configured to clamp tissue, wherein the stapling head assembly is further configured to sever and staple the clamped tissue;
   (b) a shaft assembly coupled to the stapling head assembly; and
   (c) a handle assembly coupled to the shaft assembly, wherein the handle assembly comprises:
      (i) a motor positioned within a motor housing,
      (ii) a motor housing positioner coupled to a proximal end of the motor housing, wherein the motor housing positioner is configured to translate between a proximal position and a distal position, wherein the motor is configured to translate with the motor housing positioner, and
      (iii) a selection assembly, wherein the selection assembly is operable to select between a motorized clamping motion of the stapling head assembly or a manual clamping motion of the stapling head assembly based on the position of the motor housing positioner.

2. The apparatus of claim 1, wherein the motor housing positioner comprises a rotation knob.

3. The apparatus of claim 2, wherein the rotation knob comprises splines extending distally, wherein the handle assembly comprises a housing, wherein the housing comprises teeth corresponding with the splines, wherein the splines are configured to engage the teeth during motorized operation such that the rotation knob is prevented from rotating.

4. The apparatus of claim 1, wherein the selection assembly is configured to select the motorized operation when the motor housing positioner is in the distal position, wherein the selection assembly is configured to select the manual operation when the motor housing positioned is in the proximal position.

5. The apparatus of claim 1, wherein the handle assembly further comprises a battery.

6. The apparatus of claim 5, wherein the battery is operable to supply power to the motor during motorized operation.

7. The apparatus of claim 6 further comprising spring contacts, wherein the spring contacts are operable to supply power from the battery to the motor based on the position of the motor housing positioner.

8. The apparatus of claim 1, wherein the selection assembly comprises a first gear and a second gear, wherein the first gear is coupled to the motor housing, wherein the second gear comprises splines.

9. The apparatus of claim 8, wherein the first gear is configured to engage the splines of the second gear during manual operation.

10. The apparatus of claim 8, wherein the first gear is configured to be decoupled from the splines of the second gear during motorized operation.

11. The apparatus of claim 1, wherein the shaft assembly comprises a driver actuator, wherein the driver actuator is operable to actuate the stapling head assembly.

12. The apparatus of claim 11, wherein the motor is operable to actuate the driver actuator during motorized operation.

13. The apparatus of claim 11, wherein the motor housing positioner is operable to actuate the driver actuator during manual operation.

14. The apparatus of claim 11, wherein the handle assembly comprises a firing ring, wherein the firing is operable to translate the driver actuator.

15. The apparatus of claim 14, wherein the handle assembly comprises slots, wherein the handle assembly comprises a coupling member extending through the slots to couple with the firing ring, wherein the coupling member is configured to translate through the slots to lock the longitudinal position of the firing ring.

16. An apparatus for stapling tissue, the apparatus comprising:
(a) a stapling head assembly comprising a rod;
(b) a shaft assembly coupled to the stapling head assembly; and
(c) a handle assembly coupled to the shaft assembly, wherein the handle assembly comprises:
(i) a motor,
(ii) a rotation knob, wherein the rotation knob is configured to translate between a first longitudinal position and a second longitudinal position, wherein the rotation knob is operable to translate the rod axially in a manual operational mode upon rotation of the rotation knob in the second longitudinal position, wherein the motor is operable to translate the rod axially in a motorized operational mode upon activation of the motor when the rotation knob is in the first longitudinal position, and
(iii) a selection assembly, wherein the selection assembly is operable to provide the motorized operational mode when the rotation knob is in the first longitudinal position, wherein the selection assembly is operable to provide the manual operational mode when the rotation knob is in the second longitudinal position.

17. The apparatus of claim 16, wherein the first longitudinal position of the rotation knob is a distal position, wherein the second longitudinal position of the rotation knob is a proximal position.

18. The apparatus of claim 16, wherein the rod is coupleable to an anvil, wherein the stapling head assembly is operable to clamp tissue between the anvil and the stapling head assembly, wherein the stapling head assembly comprises a knife and a plurality of staples aligned in a circular configuration, wherein the stapling head assembly is operable to drive the knife and the staples through tissue from the stapling head assembly toward the anvil.

19. An apparatus for stapling tissue, the apparatus comprising:
(a) a stapling head assembly;
(b) a shaft assembly coupled to the stapling head assembly; and
(c) a handle assembly coupled to the shaft assembly, wherein the handle assembly comprises:
(i) a motor positioned within a motor housing,
(ii) a motor housing positioner coupled to a proximal end of the motor housing, wherein the motor housing positioner is configured to translate between a proximal position and a distal position, wherein the motor is configured to translate with the motor housing positioner, and
(iii) a selection assembly, wherein the selection assembly is operable to select between a motorized axial motion of a portion of the stapling head assembly or a manual axial motion of a portion of the stapling head assembly based on the position of the motor housing positioner.

* * * * *